United States Patent
Chandrashekar et al.

(10) Patent No.: US 6,773,712 B2
(45) Date of Patent: Aug. 10, 2004

(54) PARASITIC HELMINTH CUTICLIN PROTEINS AND USES THEREOF

(75) Inventors: Ramaswamy Chandrashekar, Fort Collins, CO (US); Tony H. Morales, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 10/054,562

(22) Filed: Jan. 22, 2002

(65) Prior Publication Data

US 2002/0165375 A1 Nov. 7, 2002

Related U.S. Application Data

(62) Division of application No. 09/812,642, filed on Mar. 20, 2001, now Pat. No. 6,368,600, which is a division of application No. 09/323,427, filed on Jun. 1, 1999, now Pat. No. 6,248,329.
(60) Provisional application No. 60/087,435, filed on Jun. 1, 1998.

(51) Int. Cl.$^7$ .................... A61K 39/00; A61K 31/70; C07H 21/02; C07H 21/07
(52) U.S. Cl. .................. 424/265.1; 424/191.1; 424/185.1; 435/69.1; 435/69.3; 435/252.3; 514/44; 514/12; 514/2; 536/23.1; 536/23.2
(58) Field of Search .................. 424/93.1, 93.2, 424/130.1, 191.1, 184.1, 185.1, 266.1, 265.1, 178.1; 435/69.1, 69.3, 252.3, 320.1, 321.1; 516/2, 12, 46; 536/23.1, 23.2

(56) References Cited

U.S. PATENT DOCUMENTS 6,248,329 B1 * 6/2001 Chandrashekar et al. 424/191.1

OTHER PUBLICATIONS

Rudinger et al, in "Peptide Hormones", edited by Parsons, J.A., University Park Press, Jun. 1976, p. 6).*
Burgess et al., The Journal of Cell Biology, 111:2129□2138, 1990).*
Lazar et al., Molecular and Cellular Biology, 8(3): 247□1252, 1988.*
Jobling et al. (Mol. Microbiol. 1991, 5(7): 1755□67.*
Betschart et al., 1990, *Acta Tropica, 47*, pp. 331–338.
Bisoffi et al., 1996, *Molecular and Biochemical Parasitology, 80*, pp. 55–64.
Fujimoto et al., 1973, *Archives of Biochemistry and Biophysics, 157*, pp. 1–6.
Giorgi et al., 1997, *Mol Gen Genet, 253*, pp. 589–598.
Lassandro et al., 1994, *Molecular and Biochemical Parasitology, 65*, pp. 147–159.
Parise et al., 1997, *Biochimica et Biophysica Acta, 1337*, pp. 295–301.
Ristoratore et al., 1994, *J. Submicrosc. Cytol. Pathol., 26(3)*, pp. 437–443.
Sebastiano et al., 1991, *Developmental Biology, 146*, pp. 519–530.
Timinouni et al., 1997, *Gene, 193*, pp. 81–87.

* cited by examiner

*Primary Examiner*—Mark Navarro
*Assistant Examiner*—Padma Baskar
(74) *Attorney, Agent, or Firm*—Heska Corporation

(57) ABSTRACT

The present invention relates to: parasitic helminth cuticlin proteins; parasitic helminth cuticlin nucleic acid molecules, including those that encode such cuticlin proteins; antibodies raised against such cuticlin proteins; and compounds that inhibit parasitic helminth cuticlin activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

2 Claims, No Drawings

SEQUENCE LISTING

<160> NUMBER OF SEQ ID NOS: 18

<210> SEQ ID NO 1
<211> LENGTH: 1779
<212> TYPE: DNA
<213> ORGANISM: Dirofilaria immitis

<400> SEQUENCE: 1

```
ggtttaatta cccaagtttg aggtgtctat aacaccgact gcagcaacaa caacaaacaa      60
caaacaacaa acaacaacaa cagcaataat aaccccatca agtggaggaa gaagacagga     120
agcaatctta gttttctaa aaatcgaatt tactaaatct tctgaaatga tgattcgtct     180
tattgctttc tgtactacac ttattgcatt gtcttattcg attccggttg acaatggtgt     240
cgaaggtgag ccagaaattg aatgtggacc aacttcaata acaatcaatt ttaatacacg     300
taatgcattc gaaggacatg tttatgtgaa aggtctttat gatcaagaag gttgccgtaa     360
tgatgaaggt ggacgtcaag ttgccggaat tcacttcca tttgattcat gcaatgttgc     420
gcgtacacga tctctgaatc cacgtggtat ttttgtaaca acaactgttg tcatttcgtt     480
tcatccatta tttgttacca aagttgatcg tgcatatcga gtacaatgct tttacatgga     540
agctgataaa acagttagtg cacagattga ggtatctgaa atcacaactg cttttcaaac     600
tcaaattgtc ccgatgccag tatgccgtta tgaaattttg gatggtggac caaccggtca     660
accagttcaa tttgctatca ttggtcagcc agtttatcat aaatggacat gcgattctga     720
aaccgttgat actttctgcg cggttgtcca ttcctgcttt gtcgatgatg gtaacggtga     780
tactgtggaa attctaaatg ctgatggatg tgctcttgat aaatatttgc taaataattt     840
ggaatatcca acagatttaa tggctggcca agaagctcac gtatacaaat atgcggatcg     900
atcacagctt ttctatcaat gccagatcag tattaccatt aaagaaccaa atagcgaatg     960
tgttcgacca caatgttcag aaccacaagg attcggagct gttaaaacag gtggtgccgc    1020
agcaaaacct gctgcagctg cgcaacttcg tttactcaag aaaagatctg cagaaccgga    1080
gaatatcatt gatgtacgaa ctgatatcaa caccttgaa attagcgatg ataatcaagc    1140
tttgccagtt gatttacgtc accgtgcact tctgcaacat aatggacaac ctgtaatact    1200
tgctgcagta caaaatggaa tctgcatgtc accatttggc ttctcaatgt ttatgggttt    1260
aagcattgca ttgattgctg ccgtcattat taccatttcg tttaaatttc gtccaaatca    1320
gaaggcataa aaataatgtt agaatcatcg aagcaataat aaaactgcca tatatattcg    1380
tttcttctta tcatccttct aataactaat tttagctaac aaatatatag tatgtaggaa    1440
ataattactg taatacaata agtgatattt tcatcaaaac ttcttctatc gcttttatag    1500
cttctgaaaa gcttattcat tattcagtaa tctttatat gcatactatt gtaaatgttt    1560
catcattagg ccatgaatag tttcgtttgt tattatcatc attatcaact tgtcctattt    1620
tattctaaca gtttatcatt tgtgataata tcacaaatta taccttgtat tgcccaattt    1680
ttatgggcat catttcctat tctgtaaaca attcacttat ttgcattatt gcaattaaaa    1740
agtatttcat ttgtgaaaaa aaaaaaaaaa aaaaaaaa                            1779
```

<210> SEQ ID NO 2
<211> LENGTH: 1779
<212> TYPE: DNA
<213> ORGANISM: Dirofilaria immitis -continued

```
<400> SEQUENCE: 2
tttttttttt tttttttttt ttttcacaaa tgaaatactt tttaattgca ataatgcaaa      60
taagtgaatt gtttacagaa taggaaatga tgcccataaa aattgggcaa tacaaggtat     120
aatttgtgat attatcacaa atgataaact gttagaataa aataggacaa gttgataatg     180
atgataataa caaacgaaac tattcatggc ctaatgatga acatttaca atagtatgca      240 tataaaagat tactgaataa tgaataagct tttcagaagc tataaaagcg atagaagaag     300
ttttgatgaa aatatcactt attgtattac agtaattatt tcctacatac tatatatttg     360
ttagctaaaa ttagttatta gaaggatgat aagaagaaac gaatatatat ggcagtttta     420
ttattgcttc gatgattcta acattatttt tatgccttct gatttggacg aaatttaaac     480
gaaatggtaa taatgacggc agcaatcaat gcatgctta acccataaa cattgagaag      540 ccaaatggtg acatgcagat tccatttgt actgcagcaa gtattacagg ttgtccatta     600
tgttgcagaa gtgcacggtg acgtaaatca actggcaaag cttgattatc atcgctaatt     660
tcaagggtgt tgatatcagt tcgtacatca atgatattct ccggttctgc agatcttttc     720
ttgagtaaac gaagttgcgc agctgcagca ggttttgctg cggcaccacc tgttttaaca     780
gctccgaatc cttgtggttc tgaacattgt ggtcgaacac attcgctatt ggttcttta     840 atggtaatac tgatctggca ttgatagaaa agctgtgatc gatccgcata tttgtatacg     900
tgagcttctt ggccagccat taaatctgtt ggatattcca aattatttag caaatattta     960
tcaagagcac atccatcagc atttagaatt tccacagtat caccgttacc atcatcgaca    1020
aagcaggaat ggacaaccgc gcagaaagta tcaacggttt cagaatcgca tgtccattta    1080
tgataaactg gctgaccaat gatagcaaat tgaactggtt gaccggttgg tccaccatcc    1140
aaaatttcat aacggcatac tggcatcggg acaatttgag tttgaaaagc agttgtgatt    1200
tcagatacct caatctgtgc actaactgtt ttatcagctt ccatgtaaaa gcattgtact    1260
cgatatgcac gatcaacttt ggtaacaaat aatggatgaa acgaaatgac aacagttgtt    1320
gttacaaaaa taccacgtgg attcagagat cgtgtacgcg caacattgca tgaatcaaat    1380
ggaagtgaaa ttccggcaac ttgacgtcca ccttcatcat tacggcaacc ttcttgatca    1440
taaagacctt tcacataaac atgtccttcg aatgcattac gtgtattaaa attgattgtt    1500
attgaagttg gtccacattc aatttctggc tcaccttcga caccattgtc aaccggaatc    1560
gaataagaca atgcaataag tgtagtacag aaagcaataa gacgaatcat catttcagaa    1620
gatttagtaa attcgatttt tagaaaaact aagattgctt cctgtcttct tcctccactt    1680
gatgggghta ttattgctgt tgttgttgtt tgttgtttgt tgtttgttgt tgttgctgca    1740
gtcggtgtta tagacacctc aaacttgggt aattaaacc                           1779

<210> SEQ ID NO 3
<211> LENGTH: 1161
<212> TYPE: DNA
<213> ORGANISM: Dirofilaria immitis
<220> FEATURE:
<221> NAME/KEY: CDS
<222> LOCATION: (1)..(1161)
<223> OTHER INFORMATION:

<400> SEQUENCE: 3 atg atg att cgt ctt att gct ttc tgt act aca ctt att gca ttg tct    48
Met Met Ile Arg Leu Ile Ala Phe Cys Thr Thr Leu Ile Ala Leu Ser
 1               5                  10                  15
```

```
tat tcg att ccg gtt gac aat ggt gtc gaa ggt gag cca gaa att gaa     96
Tyr Ser Ile Pro Val Asp Asn Gly Val Glu Gly Glu Pro Glu Ile Glu
        20                  25                  30 tgt gga cca act tca ata aca atc aat ttt aat aca cgt aat gca ttc    144
Cys Gly Pro Thr Ser Ile Thr Ile Asn Phe Asn Thr Arg Asn Ala Phe
            35                  40                  45 gaa gga cat gtt tat gtg aaa ggt ctt tat gat caa gaa ggt tgc cgt    192
Glu Gly His Val Tyr Val Lys Gly Leu Tyr Asp Gln Glu Gly Cys Arg
    50                  55                  60 aat gat gaa ggt gga cgt caa gtt gcc gga att tca ctt cca ttt gat    240
Asn Asp Glu Gly Gly Arg Gln Val Ala Gly Ile Ser Leu Pro Phe Asp
65                  70                  75                  80 tca tgc aat gtt gcg cgt aca cga tct ctg aat cca cgt ggt att ttt    288
Ser Cys Asn Val Ala Arg Thr Arg Ser Leu Asn Pro Arg Gly Ile Phe
                85                  90                  95 gta aca aca act gtt gtc att tcg ttt cat cca tta ttt gtt acc aaa    336
Val Thr Thr Thr Val Val Ile Ser Phe His Pro Leu Phe Val Thr Lys
            100                 105                 110 gtt gat cgt gca tat cga gta caa tgc ttt tac atg gaa gct gat aaa    384
Val Asp Arg Ala Tyr Arg Val Gln Cys Phe Tyr Met Glu Ala Asp Lys
        115                 120                 125 aca gtt agt gca cag att gag gta tct gaa atc aca act gct ttt caa    432
Thr Val Ser Ala Gln Ile Glu Val Ser Glu Ile Thr Thr Ala Phe Gln
    130                 135                 140 act caa att gtc ccg atg cca gta tgc cgt tat gaa att ttg gat ggt    480
Thr Gln Ile Val Pro Met Pro Val Cys Arg Tyr Glu Ile Leu Asp Gly
145                 150                 155                 160 gga cca acc ggt caa cca gtt caa ttt gct atc att ggt cag cca gtt    528
Gly Pro Thr Gly Gln Pro Val Gln Phe Ala Ile Ile Gly Gln Pro Val
                165                 170                 175 tat cat aaa tgg aca tgc gat tct gaa acc gtt gat act ttc tgc gcg    576
Tyr His Lys Trp Thr Cys Asp Ser Glu Thr Val Asp Thr Phe Cys Ala
            180                 185                 190 gtt gtc cat tcc tgc ttt gtc gat gat ggt aac ggt gat act gtg gaa    624
Val Val His Ser Cys Phe Val Asp Asp Gly Asn Gly Asp Thr Val Glu
        195                 200                 205 att cta aat gct gat gga tgt gct ctt gat aaa tat ttg cta aat aat    672
Ile Leu Asn Ala Asp Gly Cys Ala Leu Asp Lys Tyr Leu Leu Asn Asn
    210                 215                 220 ttg gaa tat cca aca gat tta atg gct ggc caa gaa gct cac gta tac    720
Leu Glu Tyr Pro Thr Asp Leu Met Ala Gly Gln Glu Ala His Val Tyr
225                 230                 235                 240 aaa tat gcg gat cga tca cag ctt ttc tat caa tgc cag atc agt att    768
Lys Tyr Ala Asp Arg Ser Gln Leu Phe Tyr Gln Cys Gln Ile Ser Ile
                245                 250                 255 acc att aaa gaa cca aat agc gaa tgt gtt cga cca caa tgt tca gaa    816
Thr Ile Lys Glu Pro Asn Ser Glu Cys Val Arg Pro Gln Cys Ser Glu
            260                 265                 270 cca caa gga ttc gga gct gtt aaa aca ggt ggt gcc gca gca aaa cct    864
Pro Gln Gly Phe Gly Ala Val Lys Thr Gly Gly Ala Ala Ala Lys Pro
        275                 280                 285 gct gca gct gcg caa ctt cgt tta ctc aag aaa aga tct gca gaa ccg    912
Ala Ala Ala Ala Gln Leu Arg Leu Leu Lys Lys Arg Ser Ala Glu Pro
    290                 295                 300 gag aat atc att gat gta cga act gat atc aac acc ctt gaa att agc    960
Glu Asn Ile Ile Asp Val Arg Thr Asp Ile Asn Thr Leu Glu Ile Ser
305                 310                 315                 320 gat gat aat caa gct ttg cca gtt gat tta cgt cac cgt gca ctt ctg   1008
Asp Asp Asn Gln Ala Leu Pro Val Asp Leu Arg His Arg Ala Leu Leu
                325                 330                 335
```

```
caa cat aat gga caa cct gta ata ctt gct gca gta caa aat gga atc    1056
Gln His Asn Gly Gln Pro Val Ile Leu Ala Ala Val Gln Asn Gly Ile
        340                 345                 350 tgc atg tca cca ttt ggc ttc tca atg ttt atg ggt tta agc att gca    1104
Cys Met Ser Pro Phe Gly Phe Ser Met Phe Met Gly Leu Ser Ile Ala
    355                 360                 365 ttg att gct gcc gtc att att acc att tcg ttt aaa ttt cgt cca aat    1152
Leu Ile Ala Ala Val Ile Ile Thr Ile Ser Phe Lys Phe Arg Pro Asn
370                 375                 380 cag aag gca                                                        1161
Gln Lys Ala
385
```

<210> SEQ ID NO 4
<211> LENGTH: 387
<212> TYPE: PRT
<213> ORGANISM: Dirofilaria immitis

<400> SEQUENCE: 4

```
Met Met Ile Arg Leu Ile Ala Phe Cys Thr Thr Leu Ile Ala Leu Ser
1               5                   10                  15

Tyr Ser Ile Pro Val Asp Asn Gly Val Glu Gly Glu Pro Glu Ile Glu
            20                  25                  30

Cys Gly Pro Thr Ser Ile Thr Ile Asn Phe Asn Thr Arg Asn Ala Phe
        35                  40                  45

Glu Gly His Val Tyr Val Lys Gly Leu Tyr Asp Gln Glu Gly Cys Arg
    50                  55                  60

Asn Asp Glu Gly Gly Arg Gln Val Ala Gly Ile Ser Leu Pro Phe Asp
65                  70                  75                  80

Ser Cys Asn Val Ala Arg Thr Arg Ser Leu Asn Pro Arg Gly Ile Phe
                85                  90                  95

Val Thr Thr Thr Val Val Ile Ser Phe His Pro Leu Phe Val Thr Lys
            100                 105                 110

Val Asp Arg Ala Tyr Arg Val Gln Cys Phe Tyr Met Glu Ala Asp Lys
        115                 120                 125

Thr Val Ser Ala Gln Ile Glu Val Ser Glu Ile Thr Thr Ala Phe Gln
    130                 135                 140

Thr Gln Ile Val Pro Met Pro Val Cys Arg Tyr Glu Ile Leu Asp Gly
145                 150                 155                 160

Gly Pro Thr Gly Gln Pro Val Gln Phe Ala Ile Ile Gly Gln Pro Val
                165                 170                 175

Tyr His Lys Trp Thr Cys Asp Ser Glu Thr Val Asp Thr Phe Cys Ala
            180                 185                 190

Val Val His Ser Cys Phe Val Asp Asp Gly Asn Gly Asp Thr Val Glu
        195                 200                 205

Ile Leu Asn Ala Asp Gly Cys Ala Leu Asp Lys Tyr Leu Leu Asn Asn
    210                 215                 220

Leu Glu Tyr Pro Thr Asp Leu Met Ala Gly Gln Glu Ala His Val Tyr
225                 230                 235                 240

Lys Tyr Ala Asp Arg Ser Gln Leu Phe Tyr Gln Cys Gln Ile Ser Ile
                245                 250                 255

Thr Ile Lys Glu Pro Asn Ser Glu Cys Val Arg Pro Gln Cys Ser Glu
            260                 265                 270

Pro Gln Gly Phe Gly Ala Val Lys Thr Gly Gly Ala Ala Lys Pro
        275                 280                 285
```

```
Ala Ala Ala Ala Gln Leu Arg Leu Leu Lys Lys Arg Ser Ala Glu Pro
    290                 295                 300

Glu Asn Ile Ile Asp Val Arg Thr Asp Ile Asn Thr Leu Glu Ile Ser
305                 310                 315                 320

Asp Asp Asn Gln Ala Leu Pro Val Asp Leu Arg His Arg Ala Leu Leu
                325                 330                 335

Gln His Asn Gly Gln Pro Val Ile Leu Ala Ala Val Gln Asn Gly Ile
                340                 345                 350

Cys Met Ser Pro Phe Gly Phe Ser Met Phe Met Gly Leu Ser Ile Ala
                355                 360                 365

Leu Ile Ala Ala Val Ile Ile Thr Ile Ser Phe Lys Phe Arg Pro Asn
    370                 375                 380

Gln Lys Ala
385

<210> SEQ ID NO 5
<211> LENGTH: 1161
<212> TYPE: DNA
<213> ORGANISM: Dirofilaria immitis

<400> SEQUENCE: 5
tgccttctga tttggacgaa atttaaacga aatggtaata atgacggcag caatcaatgc      60
aatgcttaaa cccataaaca ttgagaagcc aaatggtgac atgcagattc cattttgtac     120
tgcagcaagt attacaggtt gtccattatg ttgcagaagt gcacggtgac gtaaatcaac     180
tggcaaagct tgattatcat cgctaatttc aagggtgttg atatcagttc gtacatcaat     240
gatattctcc ggttctgcag atcttttctt gagtaaacga agttgcgcag ctgcagcagg     300
ttttgctgcg gcaccacctg ttttaacagc tccgatcct tgtggttctg aacattgtgg      360
tcgaacacat tcgctatttg gttctttaat ggtaatactg atctggcatt gatagaaaag     420
ctgtgatcga tccgcatatt tgtatacgtg agcttcttgg ccagccatta aatctgttgg     480
atattccaaa ttatttagca aatatttatc aagagcacat ccatcagcat ttagaatttc     540
cacagtatca ccgttaccat catcgacaaa gcaggaatgg acaaccgcgc agaaagtatc     600
aacggtttca gaatcgcatg tccatttatg ataaactggc tgaccaatga tagcaaattg     660
aactggttga ccggttggtc caccatccaa aatttcataa cggcatactg gcatcgggac     720
aatttgagtt tgaaaagcag ttgtgatttc agatacctca atctgtgcac taactgtttt     780
atcagcttcc atgtaaaagc attgtactcg atatgcacga tcaactttgg taacaaataa     840
tggatgaaac gaaatgacaa cagttgttgt tacaaaaata ccacgtggat tcagagatcg     900
tgtacgcgca acattgcatg aatcaaatgg aagtgaaatt ccgcaacttg acgtccacc     960 ttcatcatta cggcaacctt cttgatcata aagacctttc acataaacat gtccttcgaa    1020
tgcattacgt gtattaaaat tgattgttat tgaagttggt ccacattcaa tttctggctc    1080
accttcgaca ccattgtcaa ccggaatcga ataagacaat gcaataagtg tagtacagaa    1140
agcaataaga cgaatcatca t                                              1161

<210> SEQ ID NO 6
<211> LENGTH: 1372
<212> TYPE: DNA
<213> ORGANISM: Dirofilaria immitis
```

<400> SEQUENCE: 6

```
ggtttaatta cccaagtttg aggcacatgc aattatcatt attctccttg ttattcctac      60
ttttctactt gacctacgta tcatcgatcc ctattgacaa tggtgtcgaa ggtgaacctg     120
aaatagaatg tggcgcagct tcgataacaa tcaatttcaa tactagaaat acatttgaag     180
gacacgtata tgtaaaagga ctctatgatc aggatgaatg tcgttcagat agtaatggac     240
ggcaggtagc tggaatcgaa ttggcaatgg attcgtgtaa tgttgaacga tcacgatcct     300
taaatcctcg tggtgttttt gtaacaactg tagttgtcat tacatttcat ccaaaattcg     360
ttacaaaaat agatcgagca tatcgtatac aatgttttta tatggaaagc tgataagacc     420
gttagtactg gtccttgaag tatctgaaat gactacagca ttccaaactc aagtggtacc     480
aatgcccgta tgtcgatatg agattttgga aggtggacca actggtgcac ctgttcgatt     540
tgcaatgatt ggagatcatg tatatcacaa atggacatgt gattcagaga ctacagatac     600
attctgtgca ttagtacatt catgtgttgt ggatgatgga aaaggtgatg cagtggagat     660
tctgaatgaa gaaggatgtg ctttggacaa atatttactc aataatttgg aatatattac     720
agatttaatg gctggccaag aagctcatgt ttataaatat gcagatcgat cagaactttta     780
ctatcaatgc cagattagta taacaattaa agagccacat agcgaatgtc ctcgaccaca     840
atgcacagag ccacaaggat tggtgccat aaaatctgga caaggatttg ctgctgtaaa     900
atctgctgct gcaccagctc cagaagcttc cttgctttct ccacgattga tcaagaagcg     960
atcaattaat tctgataata cggtggacgt cagtaccggt tttagcacgg ttgatataac    1020
cgaagagaat ccgaacttct cagcaaatcg tttatcatca tcaacgagcc gtgaacaatt    1080
caatggtatc ttctgtattg catcaaatga tattttactt atcatttttgt tcggtgctat    1140
gttagctatt gcttgcatat ttttaccgc ttttcttgtt cattccaata atcattctaa    1200
atcatagttc tattcgatct tatcaataat tcttaccggt ttcgagattt tagaagagag    1260
agagagagaa agagagaaag agagggaaag agagaaagag agagaaagag agagagagag    1320
agaagaaaaa agtactcgga tatttcaaaa aaaaaaaaaa aaaaaaaaaa aa            1372
```

<210> SEQ ID NO 7
<211> LENGTH: 1372
<212> TYPE: DNA
<213> ORGANISM: Dirofilaria immitis

<400> SEQUENCE: 7

```
tttttttttt tttttttttt tttttgaaaa tatccgagta cttttttcttt ctctctctct     60
ctctctttct ctctctttct ctctttccct ctctttctct ctttctctct ctctctcttc    120
taaaatctcg aaaccggtaa gaattattga taagatcgaa tagaactatg atttagaatg    180
attattggaa tgaacaagaa aagcggtaaa aaatatgcaa gcaatagcta acatagcacc    240
gaacaaaatg ataagtaaaa tatcatttga tgcaatacag aagataccat tgaattgttc    300
acggctcgtt gatgatgata aacgatttgc tgagaagttc ggattctctt cggttatatc    360
aaccgtgcta aaaccggtac tgacgtccac cgtattatca gaattaattg atcgcttctt    420
gatcaatcgt ggagaaagca aggaagcttc tggagctggt gcagcagcag attttacagc    480
agcaaatcct tgtccagatt ttatggcacc aaatccttgt ggctctgtgc attgtggtcg    540
aggacattcg ctatgtggct ctttaattgt tatactaatc tggcattgat agtaaagttc    600
tgatcgatct gcatatttat aaacatgagc ttccttggcca gccattaaat ctgtaatata    660
ttccaaatta ttgagtaaat atttgtccaa agcacatcct tcttcattca gaatctccac    720
```

-continued

```
tgcatcacct tttccatcat ccacaacaca tgaatgtact aatgcacaga atgtatctgt    780
agtctctgaa tcacatgtcc atttgtgata tacatgatct ccaatcattg caaatcgaac    840
aggtgcacca gttggtccac cttccaaaat ctcatatcga catacgggca ttggtaccac    900
ttgagtttgg aatgctgtag tcatttcaga tacttcaagg accagtacta acggtcttat    960
cagctttcca tataaaaaca ttgtatacga tatgctcgat ctattttgt aacgaattt    1020
ggatgaaatg taatgacaac tacagttgtt acaaaaacac cacgaggatt taaggatcgt   1080
gatcgttcaa cattacacga atccattgcc aattcgattc cagctacctg ccgtccatta   1140
ctatctgaac gacattcatc ctgatcatag agtccttta catatacgtg tccttcaaat    1200
gtatttctag tattgaaatt gattgttatc gaagctgcgc cacattctat ttcaggttca   1260
ccttcgacac cattgtcaat agggatcgat gatacgtagg tcaagtagaa aagtaggaat   1320
aacaaggaga ataatgataa ttgcatgtgc ctcaaacttg ggtaattaaa cc            1372
```

<210> SEQ ID NO 8
<211> LENGTH: 813
<212> TYPE: DNA
<213> ORGANISM: Dirofilaria immitis
<220> FEATURE:
<221> NAME/KEY: CDS
<222> LOCATION: (1)..(813)
<223> OTHER INFORMATION:

<400> SEQUENCE: 8

| | | | | | | | | | | | | | | | | |
|---|---|---|---|---|---|---|---|---|---|---|---|---|---|---|---|---|
| atg | ttt | tta | tat | gga | aag | ctg | ata | aga | ccg | tta | gta | ctg | gtc | ctt | gaa | 48 |
| Met | Phe | Leu | Tyr | Gly | Lys | Leu | Ile | Arg | Pro | Leu | Val | Leu | Val | Leu | Glu | |
| 1 | | | | 5 | | | | | 10 | | | | | 15 | | |
| gta | tct | gaa | atg | act | aca | gca | ttc | caa | act | caa | gtg | gta | cca | atg | ccc | 96 |
| Val | Ser | Glu | Met | Thr | Thr | Ala | Phe | Gln | Thr | Gln | Val | Val | Pro | Met | Pro | |
| | | | 20 | | | | | 25 | | | | | 30 | | | |
| gta | tgt | cga | tat | gag | att | ttg | gaa | ggt | gga | cca | act | ggt | gca | cct | gtt | 144 |
| Val | Cys | Arg | Tyr | Glu | Ile | Leu | Glu | Gly | Gly | Pro | Thr | Gly | Ala | Pro | Val | |
| | | 35 | | | | | 40 | | | | | 45 | | | | |
| cga | ttt | gca | atg | att | gga | gat | cat | gta | tat | cac | aaa | tgg | aca | tgt | gat | 192 |
| Arg | Phe | Ala | Met | Ile | Gly | Asp | His | Val | Tyr | His | Lys | Trp | Thr | Cys | Asp | |
| | 50 | | | | | 55 | | | | | 60 | | | | | |
| tca | gag | act | aca | gat | aca | ttc | tgt | gca | tta | gta | cat | tca | tgt | gtt | gtg | 240 |
| Ser | Glu | Thr | Thr | Asp | Thr | Phe | Cys | Ala | Leu | Val | His | Ser | Cys | Val | Val | |
| 65 | | | | | 70 | | | | | 75 | | | | | 80 | |
| gat | gat | gga | aaa | ggt | gat | gca | gtg | gag | att | ctg | aat | gaa | gaa | gga | tgt | 288 |
| Asp | Asp | Gly | Lys | Gly | Asp | Ala | Val | Glu | Ile | Leu | Asn | Glu | Glu | Gly | Cys | |
| | | | | 85 | | | | | 90 | | | | | 95 | | |
| gct | ttg | gac | aaa | tat | tta | ctc | aat | aat | ttg | gaa | tat | att | aca | gat | tta | 336 |
| Ala | Leu | Asp | Lys | Tyr | Leu | Leu | Asn | Asn | Leu | Glu | Tyr | Ile | Thr | Asp | Leu | |
| | | | 100 | | | | | 105 | | | | | 110 | | | |
| atg | gct | ggc | caa | gaa | gct | cat | gtt | tat | aaa | tat | gca | gat | cga | tca | gaa | 384 |
| Met | Ala | Gly | Gln | Glu | Ala | His | Val | Tyr | Lys | Tyr | Ala | Asp | Arg | Ser | Glu | |
| | | 115 | | | | | 120 | | | | | 125 | | | | |
| ctt | tac | tat | caa | tgc | cag | att | agt | ata | aca | att | aaa | gag | cca | cat | agc | 432 |
| Leu | Tyr | Tyr | Gln | Cys | Gln | Ile | Ser | Ile | Thr | Ile | Lys | Glu | Pro | His | Ser | |
| | 130 | | | | | 135 | | | | | 140 | | | | | |
| gaa | tgt | cct | cga | cca | caa | tgc | aca | gag | cca | caa | gga | ttt | ggt | gcc | ata | 480 |
| Glu | Cys | Pro | Arg | Pro | Gln | Cys | Thr | Glu | Pro | Gln | Gly | Phe | Gly | Ala | Ile | |
| 145 | | | | | 150 | | | | | 155 | | | | | 160 | |
| aaa | tct | gga | caa | gga | ttt | gct | gct | gta | aaa | tct | gct | gct | gca | cca | gct | 528 |
| Lys | Ser | Gly | Gln | Gly | Phe | Ala | Ala | Val | Lys | Ser | Ala | Ala | Ala | Pro | Ala | |
| | | | | 165 | | | | | 170 | | | | | 175 | | |

-continued

| | | |
|---|---|---|
| cca gaa gct tcc ttg ctt tct cca cga ttg atc aag aag cga tca att<br>Pro Glu Ala Ser Leu Leu Ser Pro Arg Leu Ile Lys Lys Arg Ser Ile<br>         180                      185                  190 | 576 |
| aat tct gat aat acg gtg gac gtc agt acc ggt ttt agc acg gtt gat<br>Asn Ser Asp Asn Thr Val Asp Val Ser Thr Gly Phe Ser Thr Val Asp<br>      195                    200                  205 | 624 |
| ata acc gaa gag aat ccg aac ttc tca gca aat cgt tta tca tca tca<br>Ile Thr Glu Glu Asn Pro Asn Phe Ser Ala Asn Arg Leu Ser Ser Ser<br>210                      215                  220 | 672 |
| acg agc cgt gaa caa ttc aat ggt atc ttc tgt att gca tca aat gat<br>Thr Ser Arg Glu Gln Phe Asn Gly Ile Phe Cys Ile Ala Ser Asn Asp<br>225                  230                235              240 | 720 |
| att tta ctt atc att ttg ttc ggt gct atg tta gct att gct tgc ata<br>Ile Leu Leu Ile Ile Leu Phe Gly Ala Met Leu Ala Ile Ala Cys Ile<br>               245                250                255 | 768 |
| ttt ttt acc gct ttt ctt gtt cat tcc aat aat cat tct aaa tca<br>Phe Phe Thr Ala Phe Leu Val His Ser Asn Asn His Ser Lys Ser<br>      260                  265                270 | 813 |

<210> SEQ ID NO 9
<211> LENGTH: 271
<212> TYPE: PRT
<213> ORGANISM: Dirofilaria immitis

<400> SEQUENCE: 9

Met Phe Leu Tyr Gly Lys Leu Ile Arg Pro Leu Val Leu Val Leu Glu
1               5                   10                  15

Val Ser Glu Met Thr Thr Ala Phe Gln Thr Gln Val Val Pro Met Pro
            20                  25                  30

Val Cys Arg Tyr Glu Ile Leu Glu Gly Gly Pro Thr Gly Ala Pro Val
        35                  40                  45

Arg Phe Ala Met Ile Gly Asp His Val Tyr His Lys Trp Thr Cys Asp
    50                  55                  60

Ser Glu Thr Thr Asp Thr Phe Cys Ala Leu Val His Ser Cys Val Val
65                  70                  75                  80

Asp Asp Gly Lys Gly Asp Ala Val Glu Ile Leu Asn Glu Glu Gly Cys
                85                  90                  95

Ala Leu Asp Lys Tyr Leu Leu Asn Asn Leu Glu Tyr Ile Thr Asp Leu
            100                 105                 110

Met Ala Gly Gln Glu Ala His Val Tyr Lys Tyr Ala Asp Arg Ser Glu
        115                 120                 125

Leu Tyr Tyr Gln Cys Gln Ile Ser Ile Thr Ile Lys Glu Pro His Ser
    130                 135                 140

Glu Cys Pro Arg Pro Gln Cys Thr Glu Pro Gln Gly Phe Gly Ala Ile
145                 150                 155                 160

Lys Ser Gly Gln Gly Phe Ala Ala Val Lys Ser Ala Ala Pro Ala
                165                 170                 175

Pro Glu Ala Ser Leu Leu Ser Pro Arg Leu Ile Lys Lys Arg Ser Ile
            180                 185                 190

Asn Ser Asp Asn Thr Val Asp Val Ser Thr Gly Phe Ser Thr Val Asp
        195                 200                 205

Ile Thr Glu Glu Asn Pro Asn Phe Ser Ala Asn Arg Leu Ser Ser Ser
    210                 215                 220

Thr Ser Arg Glu Gln Phe Asn Gly Ile Phe Cys Ile Ala Ser Asn Asp
225                 230                 235                 240

```
Ile Leu Leu Ile Ile Leu Phe Gly Ala Met Leu Ala Ile Ala Cys Ile
                245                 250                 255

Phe Phe Thr Ala Phe Leu Val His Ser Asn Asn His Ser Lys Ser
            260                 265                 270
```

<210> SEQ ID NO 10
<211> LENGTH: 813
<212> TYPE: DNA
<213> ORGANISM: Dirofilaria immitis

<400> SEQUENCE: 10

```
tgatttagaa tgattattgg aatgaacaag aaaagcggta aaaaatatgc aagcaatagc    60
taacatagca ccgaacaaaa tgataagtaa aatatcattt gatgcaatac agaagatacc   120
attgaattgt tcacggctcg ttgatgatga taaacgattt gctgagaagt tcggattctc   180
ttcggttata tcaaccgtgc taaaaccggt actgacgtcc accgtattat cagaattaat   240
tgatcgcttc ttgatcaatc gtggagaaag caaggaagct tctggagctg gtgcagcagc   300
agattttaca gcagcaaatc cttgtccaga ttttatggca ccaaatcctt gtggctctgt   360
gcattgtggt cgaggacatt cgctatgtgg ctctttaatt gttatactaa tctggcattg   420
atagtaaagt tctgatcgat ctgcatattt ataaacatga gcttcttggc cagccattaa   480
atctgtaata tattccaaat tattgagtaa atatttgtcc aaagcacatc cttcttcatt   540
cagaatctcc actgcatcac cttttccatc atccacaaca catgaatgta ctaatgcaca   600
gaatgtatct gtagtctctg aatcacatgt ccatttgtga tatacatgat ctccaatcat   660
tgcaaatcga acaggtgcac cagttggtcc accttccaaa atctcatatc gacatacggg   720
cattggtacc acttgagttt ggaatgctgt agtcatttca gatacttcaa ggaccagtac   780
taacggtctt atcagctttc catataaaaa cat                                813
```

<210> SEQ ID NO 11
<211> LENGTH: 34
<212> TYPE: DNA
<213> ORGANISM: Artificial sequence
<220> FEATURE:
<223> OTHER INFORMATION: Synthetic Primer

<400> SEQUENCE: 11

```
ggctggccaa gaagctcacg tatacaaata tgcg                                34
```

<210> SEQ ID NO 12
<211> LENGTH: 34
<212> TYPE: DNA
<213> ORGANISM: Artificial sequence
<220> FEATURE:
<223> OTHER INFORMATION: Synthetic Primer

<400> SEQUENCE: 12

```
cgcatatttg tatacgtgag cttcttggcc agcc                                34
```

<210> SEQ ID NO 13
<211> LENGTH: 22
<212> TYPE: DNA
<213> ORGANISM: Artificial sequence
<220> FEATURE:
<223> OTHER INFORMATION: Synthetic Primer

<400> SEQUENCE: 13

```
ggtttaatta cccaagtttg ag                                             22
```

```
<210> SEQ ID NO 14
<211> LENGTH: 27
<212> TYPE: DNA
<213> ORGANISM: Artificial sequence
<220> FEATURE:
<223> OTHER INFORMATION: Synthetic Primer

<400> SEQUENCE: 14
ccatcctaat acgactcact atagggc                                              27

<210> SEQ ID NO 15
<211> LENGTH: 41
<212> TYPE: DNA
<213> ORGANISM: Artificial sequence
<220> FEATURE:
<223> OTHER INFORMATION: Synthetic Primer

<400> SEQUENCE: 15
ggttatatca accgtgctaa aaccggtact gacgtccacc g                              41

<210> SEQ ID NO 16
<211> LENGTH: 892
<212> TYPE: DNA
<213> ORGANISM: Brugia malayi
<220> FEATURE:
<221> NAME/KEY: CDS
<222> LOCATION: (158)..(892)
<223> OTHER INFORMATION:

<400> SEQUENCE: 16
ggtttaatta cccaagtttg agatcattaa aattgatcat caataattca ataatttgtt          60
gcaatttcaa attaatcatt ttgctaattc tattattcca actattttca tcactaatca         120
ctgagaagaa atcaggaaga aagaagcaaa agttaa atg ttg cat atg caa att           175
                                        Met Leu His Met Gln Ile
                                         1               5 tgc tca ttt ttg tca tat atg ata ata gca agt att aat gct att cca           223
Cys Ser Phe Leu Ser Tyr Met Ile Ile Ala Ser Ile Asn Ala Ile Pro
                10                  15                  20 att gat aat ggt gtc gaa agt gaa cct gaa att gaa tgt ggt cca aca           271
Ile Asp Asn Gly Val Glu Ser Glu Pro Glu Ile Glu Cys Gly Pro Thr
            25                  30                  35 tca atc act gtt aat ttt aat act cga aat cct ttt gaa gga cat gta           319
Ser Ile Thr Val Asn Phe Asn Thr Arg Asn Pro Phe Glu Gly His Val
        40                  45                  50 tat gct aaa gga tta tac agt aat caa gat tgt cgt agt gat gaa ggt           367
Tyr Ala Lys Gly Leu Tyr Ser Asn Gln Asp Cys Arg Ser Asp Glu Gly
55                  60                  65                  70 gga cgt cag gta gcc gga ata tca tta ccg ttt gat tca tgt aat gtc           415
Gly Arg Gln Val Ala Gly Ile Ser Leu Pro Phe Asp Ser Cys Asn Val
                75                  80                  85 gca cgt aca cgt tcg tta aat cca cgt gga ata ttt gtc aca gct gtt           463
Ala Arg Thr Arg Ser Leu Asn Pro Arg Gly Ile Phe Val Thr Ala Val
            90                  95                 100 gtg gta att acg ttt cat cca cag ttt atc aca aaa gtt gat cga aca           511
Val Val Ile Thr Phe His Pro Gln Phe Ile Thr Lys Val Asp Arg Thr
       105                 110                 115 tat cga ttg caa tgc ttt tac atg gaa gct gat aag act gtt agc aca           559
Tyr Arg Leu Gln Cys Phe Tyr Met Glu Ala Asp Lys Thr Val Ser Thr
   120                 125                 130 caa att gaa gtt tcc gaa atg aca acc gta ttt gct aca caa ttg gta           607
Gln Ile Glu Val Ser Glu Met Thr Thr Val Phe Ala Thr Gln Leu Val
135                 140                 145                 150
```

-continued

| | | |
|---|---|---|
| cca atg cct gtg tgt aga tat gag att ctg gat ggt ggt cca acc gga<br>Pro Met Pro Val Cys Arg Tyr Glu Ile Leu Asp Gly Gly Pro Thr Gly<br>155                            160                        165 | | 655 |
| caa cct gtc cag tat gct aat att gga caa ccg gtt tat cat aaa tgg<br>Gln Pro Val Gln Tyr Ala Asn Ile Gly Gln Pro Val Tyr His Lys Trp<br>          170                        175                        180 | | 703 |
| aca tgt gat tct gaa aca gtt gat acc ttc tgt gct ttg gta cat tcc<br>Thr Cys Asp Ser Glu Thr Val Asp Thr Phe Cys Ala Leu Val His Ser<br>185                            190                        195 | | 751 |
| tgt ttt gtt gat gat ggc aat ggt gac agt att aat tta att aat gaa<br>Cys Phe Val Asp Asp Gly Asn Gly Asp Ser Ile Asn Leu Ile Asn Glu<br>    200                         205                        210 | | 799 |
| gaa gga tgt gca tta gat cga tat ctt cta aat aat ttg gaa tat cca<br>Glu Gly Cys Ala Leu Asp Arg Tyr Leu Leu Asn Asn Leu Glu Tyr Pro<br>215                          220                        225                        230 | | 847 |
| act gat cta atg gct ggc caa gaa gct cac gta tac aaa tat gcg<br>Thr Asp Leu Met Ala Gly Gln Glu Ala His Val Tyr Lys Tyr Ala<br>                235                        240                        245 | | 892 |

<210> SEQ ID NO 17
<211> LENGTH: 245
<212> TYPE: PRT
<213> ORGANISM: Brugia malayi

<400> SEQUENCE: 17

Met Leu His Met Gln Ile Cys Ser Phe Leu Ser Tyr Met Ile Ile Ala
1                  5                      10                    15

Ser Ile Asn Ala Ile Pro Ile Asp Asn Gly Val Glu Ser Glu Pro Glu
              20                      25                      30

Ile Glu Cys Gly Pro Thr Ser Ile Thr Val Asn Phe Asn Thr Arg Asn
                  35                      40                      45

Pro Phe Glu Gly His Val Tyr Ala Lys Gly Leu Tyr Ser Asn Gln Asp
        50                      55                      60

Cys Arg Ser Asp Glu Gly Gly Arg Gln Val Ala Gly Ile Ser Leu Pro
65                  70                      75                    80

Phe Asp Ser Cys Asn Val Ala Arg Thr Arg Ser Leu Asn Pro Arg Gly
                  85                      90                      95

Ile Phe Val Thr Ala Val Val Ile Thr Phe His Pro Gln Phe Ile
              100                      105                    110

Thr Lys Val Asp Arg Thr Tyr Arg Leu Gln Cys Phe Tyr Met Glu Ala
            115                      120                    125

Asp Lys Thr Val Ser Thr Gln Ile Glu Val Ser Glu Met Thr Thr Val
        130                      135                    140

Phe Ala Thr Gln Leu Val Pro Met Pro Val Cys Arg Tyr Glu Ile Leu
145                  150                      155                    160

Asp Gly Gly Pro Thr Gly Gln Pro Val Gln Tyr Ala Asn Ile Gly Gln
                  165                      170                    175

Pro Val Tyr His Lys Trp Thr Cys Asp Ser Glu Thr Val Asp Thr Phe
            180                      185                    190

Cys Ala Leu Val His Ser Cys Phe Val Asp Asp Gly Asn Gly Asp Ser
        195                      200                    205

Ile Asn Leu Ile Asn Glu Glu Gly Cys Ala Leu Asp Arg Tyr Leu Leu
    210                         215                      220

Asn Asn Leu Glu Tyr Pro Thr Asp Leu Met Ala Gly Gln Glu Ala His
225                  230                      235                    240

Val Tyr Lys Tyr Ala
            245

```
<210> SEQ ID NO 18
<211> LENGTH: 892
<212> TYPE: DNA
<213> ORGANISM: Brugia malayi

<400> SEQUENCE: 18
cgcatatttg tatacgtgag cttcttggcc agccattaga tcagttggat attccaaatt      60
atttagaaga tatcgatcta atgcacatcc ttcttcatta attaaattaa tactgtcacc     120
attgccatca tcaacaaaac aggaatgtac caaagcacag aaggtatcaa ctgtttcaga     180
atcacatgtc catttatgat aaaccggttg tccaatatta gcatactgga caggttgtcc     240
ggttggacca ccatccagaa tctcatatct acacacaggc attggtacca attgtgtagc     300
aaatacggtt gtcatttcgg aaacttcaat ttgtgtgcta acagtcttat cagcttccat     360
gtaaaagcat tgcaatcgat atgttcgatc aactttttgtg ataaactgtg gatgaaacgt     420
aattaccaca acagctgtga caaatattcc acgtggattt aacgaacgtg tacgtgcgac     480
attacatgaa tcaaacggta atgatattcc ggctacctga cgtccacctt catcactacg     540
acaatcttga ttactgtata atcctttagc atatacatgt ccttcaaaag gatttcgagt     600
attaaaatta acagtgattg atgttggacc acattcaatt tcaggttcac tttcgacacc     660
attatcaatt ggaatagcat taatacttgc tattatcata tatgacaaaa atgagcaaat     720
ttgcatatgc aacatttaac tttttgcttc tttcttcctg atttcttctc agtgattagt     780
gatgaaaata gttggaataa tagaattagc aaaatgatta atttgaaatt gcaacaaatt     840
attgaattat tgatgatcaa ttttaatgat ctcaaacttg ggtaattaaa cc             892
```

PARASITIC HELMINTH CUTICLIN PROTEINS AND USES THEREOF

This Application is a Divisional Application of application Ser. No. 09/812,642, filed Mar. 20, 2001, which issued as U.S. Pat. No. 6,368,600 B1 on Apr. 9, 2002, which is a Divisional of application Ser. No. 09/323,427, filed Jun. 1, 1999, which issued as U.S. Pat. No. 6,248,329 B1 on Jun. 19, 2001, each entitled "PARASITIC HELMINTH CUTICLIN NUCLEIC ACID MOLECULES AND USES THEREOF". This application claims the benefit of Provisional Application No. 60/087,435, filed Jun. 1, 1998.

FIELD OF THE INVENTION

The present invention relates to parasitic helminth cuticlin nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, inhibitors, and combinations thereof, as well as the use of these compositions to protect animals from diseases caused by parasitic helminths, such as heartworm disease.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, there is yet to be a commercially available vaccine developed for any parasitic helminth.

As an example of the complexity of parasitic helminths, the life cycle of D. immitis, the helminth that causes heartworm disease, includes a variety of life forms, each of which presents different targets, and challenges, for immunization. In a mosquito, D. immitis microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog.

In particular, heartworm disease is a major problem in dogs, which typically do not develop immunity, even upon infection (i.e., dogs can become reinfected even after being cured by chemotherapy). In addition, heartworm disease is becoming increasingly widespread in other companion animals, such as cats and ferrets. D. immitis has also been reported to infect humans. There remains a need to identify an efficacious composition that protects animals and humans against diseases caused by parasitic helminths, such as heartworm disease. Preferably, such a composition also protects animals from infection by such helminths.

The cuticle is an important part of the nematode's exoskeleton and protects the animal from the environment under a variety of conditions. In addition, it also mediates the metabolic interaction of the animal with its environment and, in parasitic nematodes, the interaction with the host and its immune system. The nematode cuticle is a complex extracellular structure that is secreted by an underlying syncytium of hypodermal cells. Recent studies have demonstrated that the cuticle of parasitic nematodes is a dynamic structure with important absorptive, secretory, and enzymatic activities, and not merely an inert protective covering as was once believed. See, for example, Lustigman, S. 1993, Parasitology Today, 9:8, 294–297. In addition, immunological studies have shown the central importance of cuticular antigens as targets for protective immune responses to parasitic nematodes. In spite of the wide recognition of the importance of the cuticle in the nematode physiology and its potential role as a target for immunoprophylaxis, relatively little is known about the biology of the cuticle of filarial parasites. Though a number of collagen genes have been characterized in filarial parasites, very little is known about the non-collagenous cuticular proteins, including cuticlin, in filarial parasites. Prior studies in C. elegans have shown that cuticlin genes are developmentally regulated and that the message for one of the C. elegans cuticlins, cut-1, is up-regulated during larval molting. Antibodies raised against a cuticlin of Ascaris cross-react with the epicuticular structures of filarial parasites indicating that components of cuticlin are immunogenic. Since cuticlin proteins are highly conserved among nematodes, but not among other organisms, they could be an important target for protective immunity to parasitic helminths.

SUMMARY OF THE INVENTION

The present invention is based on the isolation of two D. immitis nucleic acid molecule isoforms, each encoding a protein with amino acid sequence similarity to cuticlin cut-1 proteins from C. elegans and Ascaris lumbricodes.

The present invention relates to a novel product and process to protect animals against parasitic helminth infection (e.g., to prevent and/or treat such an infection). The present invention provides parasitic helminth cuticlin proteins and mimetopes thereof; parasitic helminth cuticlin nucleic acid molecules, including those that encode such proteins; antibodies raised against such cuticlin proteins (anti-parasitic helminth cuticlin antibodies); and compounds that inhibit cuticlin activity (i.e, inhibitory compounds or inhibitors).

The present invention also includes methods to obtain parasitic helminth cuticlin proteins, nucleic acid molecules, antibodies and inhibitory compounds. Also included in the present invention are therapeutic compositions comprising such proteins, nucleic acid molecules, antibodies, and inhibitory compounds, as well as use of such therapeutic compositions to protect animals from diseases caused by parasitic helminths.

One embodiment of the present invention is an isolated nucleic acid molecule that hybridizes under stringent hybridization conditions with a *Dirofilaria immitis* (*D. immitis*) or *Brugia malayi* (*B. malayi*) cuticlin gene. Such nucleic acid molecules are referred to as cuticlin nucleic acid molecules. A preferred isolated nucleic acid molecule of this embodiment includes a *D. immitis* or *B. malayi* cuticlin nucleic acid molecule. A *D. immitis* cuticlin nucleic acid molecule preferably includes nucleic acid sequence SEQ ID NO:1, SEQ ID NO:2, SEQ ID NO:3, SEQ ID NO:5, SEQ ID NO:6, SEQ ID NO:7, SEQ ID NO:8, or SEQ ID NO:10, or allelic variants of any of these sequences. A *B. malayi* cuticlin nucleic acid molecule preferably includes nucleic acid sequence SEQ ID NO:16, or SEQ ID NO:18, or allelic variants of these sequences.

Another embodiment of the present invention is an isolated nucleic acid molecule that includes a parasitic helminth cuticlin nucleic acid molecule. A preferred parasitic helminth cuticlin nucleic acid molecule of the present invention preferably includes nucleic acid sequence SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18 or allelic variants of any of these sequences.

The present invention also relates to recombinant molecules, recombinant viruses and recombinant cells that include an isolated cuticlin nucleic acid molecule of the present invention. Also included are methods to produce such nucleic acid molecules, recombinant molecules, recombinant viruses and recombinant cells.

Another embodiment of the present invention includes a non-native parasitic helminth cuticlin protein encoded by a nucleic acid molecule that hybridizes under stringent hybridization conditions with a parasitic helminth cuticlin gene. A preferred parasitic helminth protein is capable of eliciting an immune response when administered to an animal and/or of having parasitic helminth cuticlin activity. A preferred parasitic helminth cuticlin protein is encoded by a nucleic acid molecule that hybridizes under stringent conditions with a nucleic acid molecule including either SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18, or allelic variants of any of these sequences.

Another embodiment of the present invention includes a parasitic helminth cuticlin protein. A preferred cuticlin protein includes a *D. immitis* or *B. malayi* cuticlin protein. A preferred *D. immitis* cuticlin protein comprises amino acid sequence SEQ ID NO:4 or SEQ ID NO:9. A preferred *B. malayi* cuticlin protein comprises amino acid sequence SEQ ID NO:17.

The present invention also relates to: mimetopes of parasitic helminth cuticlin proteins; isolated antibodies that selectively bind to parasitic helminth cuticlin proteins or mimetopes thereof; and inhibitors of parasitic helminth cuticlin proteins or mimetopes thereof. Also included are methods, including recombinant methods, to produce proteins, mimetopes, antibodies, and inhibitors of the present invention.

Another embodiment of the present invention is a method to identify a compound capable of inhibiting parasitic helminth cuticlin activity, comprising the steps of: (a) contacting a parasitic helminth cuticlin protein with a putative inhibitory compound under conditions in which, in the absence of the compound, the protein has cuticlin activity; and (b) determining if the putative inhibitory compound inhibits the cuticlin activity. Also included in the present invention is a test kit to identify a compound capable of inhibiting parasitic helminth cuticlin activity. Such a test kit includes a parasitic helminth cuticlin protein having cuticlin activity and a means for determining the extent of inhibition of the cuticlin activity in the presence of a putative inhibitory compound.

Yet another embodiment of the present invention is a therapeutic composition that is capable of protecting an animal from disease caused by a parasitic helminth. Such a therapeutic composition includes one or more of the following protective compounds: an isolated parasitic helminth cuticlin protein or a mimetope thereof; an isolated nucleic acid molecule that hybridizes under stringent hybridization conditions with a *Dirofilaria immitis* cuticlin gene; an isolated antibody that selectively binds to a parasitic helminth cuticlin protein; or an inhibitor of cuticlin protein activity identified by its ability to inhibit parasitic helminth cuticlin activity. A preferred therapeutic composition of the present invention also includes an excipient, an adjuvant, or a carrier. Preferred cuticlin nucleic acid molecule therapeutic compositions of the present invention include genetic vaccines, recombinant virus vaccines, and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated parasitic helminth cuticlin proteins, isolated parasitic helminth cuticlin nucleic acid molecules, isolated antibodies directed against parasitic helminth cuticlin proteins, and other inhibitors of parasitic helminth cuticlin activity. As used herein, the terms isolated parasitic helminth cuticlin proteins, and isolated parasitic helminth cuticlin nucleic acid molecules refers to cuticlin proteins and cuticlin nucleic acid molecules derived from a parasitic helminths and which can be obtained from their natural source, or can be produced using, for example, recombinant nucleic acid technology or chemical synthesis. Also included in the present invention is the use of these proteins, nucleic acid molecules, antibodies and other inhibitors as therapeutic compositions to protect animals from parasitic helminth diseases as well as in other applications, such as those disclosed below.

The present invention is based on the isolation of two cDNAs encoding cuticlin cut-1 like proteins from *D. immitis*, and the isolation of a homolog of these cDNAs from *B. malayi*. Parasitic helminth cuticlin proteins and nucleic acid molecules of the present invention have utility because they represent novel targets for anti-parasite vaccines and drugs. The products and processes of the present invention are advantageous because they enable the inhibition of parasite physiological functions that depend on cuticlin activity.

One embodiment of the present invention is an isolated protein comprising a parasitic helminth cuticlin protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. The terms "isolated" and "biologically pure" do not necessarily reflect the extent to which the protein has been purified. An isolated protein of the present invention can be obtained from its natural source, can be produced using recombinant DNA technology or can be produced by chemical synthesis. When an isolated protein of the present invention is produced using recombinant DNA technology or produced by chemical synthesis, the protein is referred to herein as either an isolated protein or as a non-native protein.

As used herein, an isolated parasitic helminth cuticlin protein can be a full-length protein or any homolog of such a protein. An isolated protein of the present invention, including a homolog, can be identified in a straight-forward manner by the protein's ability to elicit an immune response against a parasitic helminth cuticlin protein or to catalyze the cleavage of asparagine to aspartic acid and ammonia. Examples of parasitic helminth cuticlin homologs include parasitic helminth cuticlin proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation, or addition of glycerophosphatidyl inositol) so that the homolog includes at least one epitope capable of eliciting an immune response against a parasitic helminth cuticlin protein. That is, when the homolog is administered to an animal as an immunogen, using techniques known to those skilled in the art, the animal will produce an immune response against at least one epitope of a natural parasitic helminth cuticlin protein. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four amino acids. The ability of a protein to effect an immune response can be measured using techniques known to those skilled in the art.

Parasitic helminth cuticlin protein homologs can be the result of natural allelic variation or natural mutation. Parasitic helminth cuticlin protein homologs of the present invention can also be produced using techniques known in the art including, but not limited to, direct modifications to the protein or modifications to the gene encoding the protein using, for example, classic or recombinant DNA techniques to effect random or targeted mutagenesis.

A cuticlin protein of the present invention is encoded by a parasitic helminth cuticlin nucleic acid molecule. As used herein, a parasitic helminth cuticlin nucleic acid molecule includes a nucleic acid sequence related to a natural parasitic helminth cuticlin gene, and preferably, to a *D. immitis* or *B. malayi* cuticlin gene. As used herein, a parasitic helminth cuticlin gene includes all regions that control production of the parasitic helminth cuticlin protein encoded by the gene (such as, but not limited to, transcription, translation or post-translation control regions) as well as the coding region itself, and any introns or non-translated coding regions. As used herein, a gene that "includes" or "comprises" a nucleic acid sequence may include that sequence in one contiguous array, or may include that sequence as fragmented exons. As used herein, the term "coding region" refers to a continuous linear array of nucleotides that translates into a protein. A full-length coding region is that coding region which is translated into a full-length, i.e., a complete, protein as would be initially translated in its natural milieu, prior to any post-translational modifications.

In one embodiment, a parasitic helminth cuticlin gene of the present invention includes the nucleic acid molecule represented by the nucleic acid sequence SEQ ID NO:1 (the coding strand), as well as the complement of SEQ ID NO:1. The production of this molecule (also referred to herein as nDiCut-1A) is disclosed in the Examples. The complement of SEQ ID NO:1 (represented herein by SEQ ID NO:2) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited.

In another embodiment, a parasitic helminth cuticlin gene of the present invention includes the nucleic acid sequence SEQ ID NO:6, as well as the complement of SEQ ID NO:6. Nucleic acid sequence SEQ ID NO:6 represents the nucleic acid sequence of the coding strand of the nucleic acid molecule denoted herein as nDiCut-1B, the production of which is disclosed in the Examples. The complement of SEQ ID NO:6 (represented herein by SEQ ID NO:7) refers to the nucleic acid sequence of the strand complementary to the strand having SEQ ID NO:6.

In another embodiment, a parasitic helminth cuticlin gene of the present invention includes the nucleic acid sequence SEQ ID NO:16, as well as the complement of SEQ ID NO:16. Nucleic acid sequence SEQ ID NO:16 represents the nucleic acid sequence of the coding strand of the nucleic acid molecule denoted herein as BmCut-1A, the production of which is disclosed in the Examples. The complement of SEQ ID NO:16 (represented herein by SEQ ID NO:18) refers to the nucleic acid sequence of the strand complementary to the strand having SEQ ID NO:16.

In another embodiment, a parasitic helminth cuticlin gene can be an allelic variant that includes a similar, but not identical, sequence to SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18. For example, an allelic variant of a parasitic helminth cuticlin gene including SEQ ID NO:1 and SEQ ID NO:2 is a gene that occurs at essentially the same locus (or loci) in the genome as the gene including SEQ ID NO:1 and SEQ ID NO:2, but which, due to natural variations caused by, for example, mutation or recombination, has a similar but not identical sequence. Because natural selection typically selects against alterations that affect function, an allelic variant usually encodes a protein having a similar activity or function to that of the protein encoded by the gene to which it is being compared. An allelic variant of a gene or nucleic acid molecule can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found naturally occurring within parasitic helminths because the helminth genome is diploid, and sexual reproduction will result in the reassortment of alleles.

In one embodiment of the present invention, an isolated cuticlin protein is encoded by a nucleic acid molecule that hybridizes under stringent hybridization conditions to a gene encoding a parasitic helminth cuticlin protein (i.e., to a *D.*

*immitis* or *B. malayi* cuticlin gene). The minimal size of a cuticlin protein of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. The size of a nucleic acid molecule encoding such a protein is dependent on the nucleic acid composition and the percent homology between the parasitic helminth cuticlin nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a parasitic helminth cuticlin protein is typically at least about 12 to about 15 nucleotides in length if the nucleic acid molecule is GC-rich and at least about 15 to about 17 nucleotides in length if it is AT-rich. The minimal size of a nucleic acid molecule used to encode a cuticlin protein homolog of the present invention is from about 12 to about 18 nucleotides in length. Thus, the minimal size of a cuticlin protein homolog of the present invention is from about 4 to about 6 amino acids in length. There is no limit, other than a practical limit, on the maximal size of a nucleic acid molecule encoding a parasitic helminth cuticlin protein or protein homolog because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$T_m$=81.5° C.+16.6 log $M$+0.41(% $G+C$)−500/$n$−0.61(% formamide).

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$T_d$=4($G+C$)+2($A+T$).

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Stringent hybridization conditions are commonly understood by those skilled in the art to be those experimental conditions that will allow less than or equal to about 30% base pair mismatch (i.e., at least about 70% identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea nucleic acid molecule of about 150 bp in length or greater, the following conditions could preferably be used. The average G+C content of *D. immitis* DNA is about 35%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC and 0% formamide, the $T_m$ of perfect hybrids would be about 79° C.:

$$81.5° C.+16.6 \log (0.15M)+(0.41\times0.35)-(500/150)-(0.61\times0)=79° C.$$

Thus, to achieve hybridization with nucleic acid molecules having about 30% base pair mismatch, hybridization washes would be carried out at a temperature of less than or equal to 49° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 49° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. It is further known that the various available sequence analysis programs produce substantially similar results when the two compared molecules encode amino acid sequences that have greater than 30% amino acid identity. See Johnson et al., *J. Mol. Biol.*, vol. 233, pages 716–738, 1993, and Feng et al., *J. Mol. Evol.*, vol. 21, pages 112–125, 1985, both of which are incorporated by reference herein in their entirety. Preferred methods to determine the percent identity among amino acid sequences and also among nucleic acid sequences include analysis using one or more of the commercially available computer programs designed to compare and analyze nucleic acid or amino acid sequences. These computer programs include, but are in no way limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A particularly preferred method to determine the percent identity among amino acid sequences and also among nucleic acid sequences is to perform the analysis using the DNAsis™ computer program, using default parameters.

A preferred parasitic helminth cuticlin protein of the present invention is a compound that when administered to an animal in an effective manner, is capable of protecting that animal from disease caused by a parasitic helminth. In accordance with the present invention, the ability of a cuticlin protein of the present invention to protect an animal from disease by a parasitic helminth refers to the ability of that protein to, for example, treat, ameliorate or prevent disease caused by parasitic helminths. In one embodiment, a parasitic helminth cuticlin protein of the present invention can elicit an immune response (including a humoral and/or cellular immune response) against a parasitic helminth.

Suitable parasites to target include any parasite that is essentially incapable of causing disease in an animal administered a parasitic helminth cuticlin protein of the present invention. Accordingly, a parasite to target includes any parasite that produces a protein having one or more epitopes that can be targeted by a humoral or cellular immune response against a parasitic helminth cuticlin protein of the present invention or that can be targeted by a compound that otherwise inhibits parasite cuticlin activity, thereby resulting in the decreased ability of the parasite to cause disease in an animal. Preferred parasites to target include parasitic helminths such as nematodes, cestodes, and trematodes, with nematodes being preferred. Preferred nematodes to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *D. immitis* being even more preferred.

The present invention also includes mimetopes of parasitic helminth cuticlin proteins of the present invention. As used herein, a mimetope of a parasitic helminth cuticlin protein of the present invention refers to any compound that is able to mimic the activity of a parasitic helminth cuticlin protein (e.g., has the ability to elicit an immune response against a parasitic helminth cuticlin protein of the present invention or ability to inhibit parasitic helminth cuticlin activity). The ability to mimic the activity of a parasitic helminth cuticlin protein is likely to be the result of a structural similarity between the parasitic helminth cuticlin protein and the mimetope. It is to be noted, however, that the mimetope need not have a structure similar to a parasitic helminth cuticlin protein as long as the mimetope functionally mimics the protein. A mimetope can be, but is not limited to: a peptide that has been modified to decrease its susceptibility to degradation (e.g., as an all-D retro peptide); an anti-idiotypic or catalytic antibody, or a fragment thereof; a non-proteinaceous immunogenic portion of an isolated protein (e.g., a carbohydrate structure); or a synthetic or natural organic molecule, including a nucleic acid. Such a mimetope can be designed using computer-generated structures of proteins of the present invention. A mimetope can also be obtained by generating random samples of molecules, such as oligonucleotides, peptides or other organic molecules, and screening such samples by affinity chromatography techniques using the corresponding binding partner.

In one embodiment, a parasitic helminth cuticlin protein of the present invention is a fusion protein that includes a parasitic helminth cuticlin protein-containing domain attached to one or more fusion segments. Suitable fusion segments for use with the present invention include, but are not limited to, segments that can: enhance a protein's stability; act as an immunopotentiator to enhance an immune response against a parasitic helminth cuticlin protein; or assist purification of a parasitic helminth cuticlin protein (e.g., by affinity chromatography). A suitable fusion segment can be a domain of any size that has the desired function (e.g., imparts increased stability, imparts increased immunogenicity to a protein, or simplifies purification of a protein). Fusion segments can be joined to the amino or carboxyl termini of a parasitic helminth cuticlin protein-containing domain, and can be susceptible to cleavage in order to enable straight-forward recovery of a parasitic helminth cuticlin protein. A fusion protein is preferably produced by culturing a recombinant cell transformed with a fusion nucleic acid molecule that encodes a protein including a fusion segment attached to either the carboxyl or amino terminal end of a cuticlin protein-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7-tag peptide, a FLAG™ peptide, or other domain that can be purified using compounds that bind to the domain, such as monoclonal antibodies). More preferred fusion segments include metal binding domains, such as a poly-histidine segment; a maltose binding domain; a strep tag peptide, such as that available from Biometra® in Tampa, Fla.; and an S10 peptide.

In another embodiment, a parasitic helminth cuticlin protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a parasitic helminth cuticlin protein of the present invention attached to one or more compounds protective against one or more other infectious agents, particularly an agent that infects humans, cats, dogs, ferrets, cattle or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacteritim, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizoptus, Scolecobasidium, Sporothrix, Stemphyliuim, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a parasitic helminth cuticlin protein of the present invention is attached to one or more additional compounds protective against heartworm disease. In another embodiment, one or more protective compounds, such as those listed above, can be included in a multivalent vaccine comprising a parasitic helminth cuticlin protein of the present invention and one or more other protective molecules as separate compounds.

In one embodiment, a preferred isolated cuticlin protein of the present invention is a protein encoded by a nucleic acid molecule comprising at least a portion of nDiCut-1A, nDiCut-1B, or nBmCut-1A, or by an allelic variant of any of these nucleic acid molecules. Also preferred is an isolated cuticlin protein encoded by a nucleic acid molecule having the nucleic acid sequence SEQ ID NO:1, SEQ ID NO:3, SEQ ID NO:6, SEQ ID NO:8, or SEQ ID NO:16; or by an allelic variant of a nucleic acid molecule having any of these sequences.

Translation of SEQ ID NO:1, the coding strand of nucleic acid molecule nDiCut-1A, yields an essentially full length parasitic helminth cuticlin protein of 387 amino acids, referred to herein as PDiCut-1A, the amino acid sequence of which is represented by SEQ ID NO:4. The open reading frame spans from nucleotide 167 through nucleotide 1327 of SEQ ID NO:1 and a termination (stop) codon spans from nucleotide 1329 through nucleotide 1331 of SEQ ID NO:1. The coding region encoding PDiCut-1A, is represented by SEQ ID NO:3 (the coding strand) and SEQ ID NO:5 (the complementary strand).

Translation of SEQ ID NO:6, the coding strand of nucleic acid molecule nDiCut-1B, yields a full length parasitic helminth cuticlin protein of 271 amino acids, referred to herein as PDiCut-1B, the amino acid sequence of which is represented by SEQ ID NO:9, assuming an open reading frame that spans from nucleotide 392 through nucleotide 1203 of SEQ ID NO:6. The coding region encoding PDiCut-1B is represented by SEQ ID NO:8 (the coding strand) and SEQ ID NO:10 (the complementary strand). The deduced amino acid sequence is represented by SEQ ID NO:9.

Translation of SEQ ID NO:16, the coding strand of nucleic acid molecule nBmCut-1A, yields a partial length parasitic helminth cuticlin protein of 245 amino acids, referred to herein as PBmCut-1A, the amino acid sequence of which is represented by SEQ ID NO:17. The open reading frame spans from nucleotide 158 through nucleotide 892 of SEQ ID NO:16.

One embodiment of the present invention includes a non-native parasitic helminth cuticlin protein encoded by a nucleic acid molecule that hybridizes under stringent hybridization conditions with a parasitic helminth cuticlin gene. A preferred parasitic helminth cuticlin protein is capable of eliciting an immune response when administered to an animal and/or of having parasitic helminth cuticlin activity. A preferred parasitic helminth cuticlin protein is encoded by a nucleic acid molecule that hybridizes under stringent conditions with a nucleic acid molecule including either SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18, or with allelic variants of any of these sequences A preferred cuticlin protein includes a protein encoded by a nucleic acid molecule which is at least about 50 nucleotides and which hybridizes under conditions which preferably allow about 20% base pair mismatch, more preferably under conditions which allow about 15% base pair mismatch, more preferably under conditions which allow about 10% base pair mismatch, more preferably under conditions which allow about 5% base pair mismatch, and even more preferably under conditions which allow about 2% base pair mismatch with a nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18.

Another preferred cuticlin protein of the present invention includes a protein encoded by a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch, more preferably under conditions which allow about 5% base pair mismatch, and even more preferably under conditions which allow about 2% base pair mismatch with a nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18.

Another embodiment of the present invention includes a cuticlin protein encoded by a nucleic acid molecule comprising at least about 50 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18. Additional preferred cuticlin proteins include proteins encoded by oligonucleotides of an isolated nucleic acid molecule comprising at least about 50 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18, wherein said oligonucleotide comprises at least about 50 nucleotides.

Another embodiment of the present invention includes a cuticlin protein encoded by a nucleic acid molecule comprising at least about 150 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18. Additional preferred cuticlin proteins include proteins encoded by oligonucleotides of an isolated nucleic acid molecule comprising at least about 150 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18, wherein said oligonucleotide comprises at least about 50 nucleotides.

A preferred cuticlin protein of the present invention comprises a protein that is that is at least about 75%, more preferably at least about 80%, more preferably at least about 85%, more preferably at least about 90%, more preferably at least about 95%, and more preferably at least about 98% identical to identical to PDiCut-1A, PDiCut-1B, or PBmCut-1A, More preferred is a cuticlin protein comprising PDiCut-1A, PDiCut-1B, or PBmCut-1A, or a protein encoded by an allelic variant of a nucleic acid molecule encoding a protein comprising PDiCut-1A, PDiCut-1B, or PBmCut-1A.

Also preferred is a cuticlin protein comprising an amino acid sequence that is at least about 75%, more preferably at least about 80%, more preferably at least about 85%, more preferably at least about 90%, more preferably at least about 95%, and more preferably at least about 98% identical to amino acid sequence SEQ ID NO:4, SEQ ID NO:9, or SEQ ID NO:17. Even more preferred is an amino acid sequence having the sequence represented by SEQ ID NO:4, SEQ ID NO:9, or SEQ ID NO:17, or an allelic variant of any of these an amino acid sequences.

In one embodiment, a preferred parasitic helminth cuticlin protein comprises an amino acid sequence of at least about 5 amino acids, preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 50 amino acids, more preferably at least about 100 amino acids, more preferably at least about 200 amino acids, more preferably at least about 250 amino acids, more preferably at least about 275 amino acids, more preferably at least about 300 amino acids, more preferably at least about 350 amino acids, more preferably at least about 375 amino acids, and even more preferably at least about 400 amino acids. In another embodiment, preferred parasitic helminth cuticlin proteins comprise full-length proteins, i.e., proteins encoded by full-length coding regions, or post-translationally modified proteins thereof, such as mature proteins from which initiating methionine and/or signal sequences or "pro" sequences have been removed.

A fragment of a parasitic helminth cuticlin protein of the present invention preferably comprises at least about 5 amino acids, more preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 40 amino acids, more preferably at least about 45 amino acids, more preferably at least about 50 amino acids, more preferably at least about 55 amino acids, more preferably at least about 60 amino acids, more preferably at least about 65 amino acids, more preferably at least about 70 amino acids, more preferably at least about 75 amino acids, more preferably at least about 80 amino acids, more preferably at least about 85 amino acids, more preferably at least about 90 amino acids, more preferably at least about 95 amino acids, and even more preferably at least about 100 amino acids in length.

A particularly preferred parasitic helminth cuticlin protein of the present invention comprises amino acid sequence SEQ ID NO:4, including, but not limited to, a cuticlin protein consisting of amino acid sequence SEQ ID NO:4, a fusion protein or a multivalent protein; or a protein encoded by an allelic variant of a nucleic acid molecule encoding a protein having amino acid sequence SEQ ID NO:4. Also particularly preferred is a parasitic helminth cuticlin protein of the present invention that comprises amino acid sequence SEQ ID NO:9, including, but not limited to, a cuticlin protein consisting of amino acid sequence SEQ ID NO:9, a fusion protein or a multivalent protein; or a protein encoded by an allelic variant of a nucleic acid molecule encoding a protein having amino acid sequence SEQ ID NO:9. Also particularly preferred is a parasitic helminth cuticlin protein of the present invention that comprises amino acid sequence SEQ ID NO:17, including, but not limited to, a cuticlin protein consisting of amino acid sequence SEQ ID NO:17, a fusion protein or a multivalent protein; or a protein encoded by an allelic variant of a nucleic acid molecule encoding a protein having amino acid sequence SEQ ID NO:17.

Another embodiment of the present invention is an isolated nucleic acid molecule comprising a parasitic helminth cuticlin nucleic acid molecule. The identifying characteristics of such a nucleic acid molecule are heretofore described. A nucleic acid molecule of the present invention can include an isolated natural parasitic helminth cuticlin gene or a homolog thereof, the latter of which is described in more detail below. A nucleic acid molecule of the present invention can include one or more regulatory regions, a full-length or a partial coding region, or a combination thereof. The minimal size of a nucleic acid molecule of the present invention is a size sufficient to allow the formation of a stable hybrid (i.e., hybridization under stringent hybridization conditions) with the complementary sequence of another nucleic acid molecule. Accordingly, the minimal size of a cuticlin nucleic acid molecule of the present invention is from about 12 to about 18 nucleotides in length. A preferred cuticlin nucleic acid molecule includes a parasitic helminth cuticlin nucleic acid molecule.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated parasitic helminth cuticlin nucleic acid molecule of the present invention can be isolated from its natural source or produced using recombinant DNA technology (e.g., polymerase chain reaction (PCR) amplification or cloning) or chemical synthesis. Isolated parasitic helminth cuticlin nucleic acid molecules can include, for example, natural allelic variants and nucleic acid molecules modified by nucleotide insertions, deletions, substitutions, or inversions in a manner such that the modifications do not substantially interfere with the nucleic acid molecule's ability to encode a cuticlin protein of the present invention.

A parasitic helminth cuticlin nucleic acid molecule homolog can be produced using a number of methods known to those skilled in the art. See, for example, Sambrook et al., 1989, *Molecular Cloning: A Laboratory Manual*, Cold Spring Harbor Labs Press; Sambrook et al., ibid., is incorporated by reference herein in its entirety. For example, a nucleic acid molecule can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. A nucleic acid molecule homolog can be selected by hybridization with a parasitic helminth cuticlin nucleic acid molecule or by screening the function of a protein encoded by the nucleic acid molecule (e.g., ability to elicit an immune response against at least one epitope of a parasitic helminth cuticlin protein, or the ability to demonstrate cuticlin activity).

An isolated nucleic acid molecule of the present invention can include a nucleic acid sequence that encodes a parasitic helminth cuticlin protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth cuticlin protein.

A preferred nucleic acid molecule of the present invention, when administered to an animal, is capable of protecting that animal from disease caused by a parasitic helminth. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective protein (e.g., a cuticlin protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an isolated nucleic acid molecule that hybridizes under stringent hybridization conditions with a parasitic helminth cuticlin gene. Preferred parasitic helminth cuticlin genes of the present invention are cuticlin genes from *Dirofilaria immitis* or *B. malayi*. Such nucleic acid molecules are referred to as parasitic helminth cuticlin nucleic acid molecules. A parasitic helminth cuticlin gene preferably includes at least one of the following nucleic acid sequences: SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18.

In one embodiment of the present invention, a preferred parasitic helminth cuticlin nucleic acid molecule includes an isolated nucleic acid molecule which is at least about 50 nucleotides and which hybridizes under conditions which preferably allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18.

Another preferred parasitic helminth cuticlin nucleic acid molecule of the present invention includes a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18.

Another embodiment of the present invention includes a nucleic acid molecule comprising at least about 50 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18. Additional preferred nucleic acid molecules of the present invention include oligonucleotides of an isolated nucleic acid molecule comprising at least about 50 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18, wherein said oligonucleotide comprises at least about 50 nucleotides.

Another embodiment of the present invention includes a nucleic acid molecule comprising at least about 150 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18. Additional preferred nucleic acid molecules of the present invention include oligonucleotides of an isolated nucleic acid molecule comprising at least about 150 nucleotides, wherein said nucleic acid molecule hybridizes, in a solution comprising 2×SSC and 0% formamide, at a temperature of 37° C., and washing in 1×SSC and 0% formamide at a temperature of 64° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:7, SEQ ID NO:9, SEQ ID NO:10, SEQ ID NO:16, or SEQ ID NO:18, wherein said oligonucleotide comprises at least about 50 nucleotides.

In another embodiment, a parasitic helminth cuticlin nucleic acid molecule of the present invention includes a nucleic acid molecule that is at least about 70%, more preferably at least about 75%, more preferably at least about 80%, more preferably at least about 85%, more preferably at least about 90%, and even more preferably at least about 95% identical to nucleic acid molecule nDiCut-1A nDiCut-1B, or nBmCut-1A, or an allelic variant of any of these nucleic acid molecules. Also preferred is a parasitic helminth cuticlin nucleic acid molecule comprising a nucleic acid sequence that is that is at least about 70%, more preferably at least about 75%, more preferably at least about 80%, more preferably at least about 85%, more preferably at least about 90%, and even more preferably at least about 95% identical to nucleic acid sequence SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18; or an allelic variant of a nucleic acid molecule having any of these sequences.

Particularly preferred is a cuticlin nucleic acid molecule comprising all or part of nucleic acid molecule nDiCut-1A, nDiCut-1B, or nBmCut-1A, or an allelic variant of any these nucleic acid molecules. Also particularly preferred is a nucleic acid molecule that includes at least a portion of nucleic acid sequence SEQ ID NO:1, SEQ ID NO:2, SEQ ID NO:3, SEQ ID NO:5, SEQ ID NO:6, SEQ ID NO:7, SEQ ID NO:8, SEQ ID NO:10, SEQ ID NO:16, or SEQ ID NO:18, or an allelic variant of a nucleic acid molecule having any of these nucleic acid sequences. Such a nucleic acid molecule can include nucleotides in addition to those included in the SEQ ID NOs, such as, but not limited to, nucleotides comprising a full-length gene, or nucleotides comprising a nucleic acid molecule encoding a fusion protein or a nucleic acid molecule encoding a multivalent protective compound.

The present invention also includes a nucleic acid molecule encoding a protein having at least a portion of SEQ ID NO:4, or an allelic variant of a nucleic acid molecule encoding a protein having at least a portion of SEQ ID NO:4. The present invention further includes a nucleic acid molecule that has been modified to accommodate codon usage properties of a cell in which such a nucleic acid molecule is to be expressed. Also included in the present invention is a nucleic acid molecule encoding a protein having at least a portion of SEQ ID NO:9, or an allelic variant of a nucleic acid molecule encoding a protein having at least a portion of SEQ ID NO:9. The present invention further includes a nucleic acid molecule that has been modified to accommodate codon usage properties of a cell in which such a nucleic acid molecule is to be expressed. Also included in the present invention is a nucleic acid molecule encoding a protein having at least a portion of SEQ ID NO:17, or an allelic variant of a nucleic acid molecule encoding a protein having at least a portion of SEQ ID NO:17. The present invention further includes a nucleic acid molecule that has been modified to accommodate codon usage properties of a cell in which such a nucleic acid molecule is to be expressed.

In another embodiment, a preferred parasitic helminth cuticlin nucleic acid molecule of the present invention comprises a nucleic acid molecule comprising at least about 15 nucleotides, more preferably at least about 18 nucleotides, more preferably at least about 20 nucleotides, more preferably at least about 25 nucleotides, more preferably at least about 30 nucleotides, more preferably at least about 40 nucleotides, more preferably at least about 50 nucleotides, more preferably at least about 100 nucleotides, more preferably at least about 150 nucleotides, more preferably at least about 350 nucleotides, more preferably at least about 450 nucleotides, more preferably at least about 550 nucleotides, more preferably at least about 650 nucleotides, more preferably at least about 750 nucleotides, more preferably at least about 1000 nucleotides, more preferably at least about 1500 nucleotides, more preferably at least about 1750 nucleotides more preferably at least about 1775 nucleotides, and even more preferably at least about 2000 nucleotides in length.

In another embodiment, a preferred parasitic helminth cuticlin nucleic acid molecule encodes a protein comprising at least about 5 amino acids, preferably at least about 6 amino acids, more preferably at least about 10 amino acids, more preferably at least about 15 amino acids, more preferably at least about 20 amino acids, more preferably at least about 25 amino acids, more preferably at least about 30 amino acids, more preferably at least about 40 amino acids, more preferably at least about 50 amino acids, more preferably at least about 100 amino acids, more preferably at least about 150 amino acids, more preferably at least about 200 amino acids, more preferably at least about 300 amino acids, more preferably at least about 375 amino acids, and even more preferably at least about 400 amino acids in length.

Knowing the nucleic acid sequences of certain parasitic helminth cuticlin nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other parasitic helminth cuticlin nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria or B. malayi L3, L4 or adult cDNA libraries as well as genomic DNA libraries. Similarly, preferred DNA sources from which to amplify nucleic acid molecules include Dirofilaria or B. malayi L3, L4 or adult first-strand cDNA syntheses and genomic DNA. Techniques to clone and amplify genes are disclosed, for example, in Sambrook et al., ibid.

The present invention also includes a nucleic acid molecule that is an oligonucleotide capable of hybridizing, under stringent hybridization conditions, with complementary regions of other, preferably longer, nucleic acid molecules of the present invention such as those comprising parasitic helminth cuticlin nucleic acid molecules; or with complementary regions of other parasitic helminth cuticlin nucleic acid molecules. An oligonucleotide of the present invention can be RNA, DNA, or derivatives of either. The minimum size of such an oligonucleotide is the size required for formation of a stable hybrid between the oligonucleotide and a complementary sequence on another nucleic acid molecule. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit parasitic helminth cuticlin protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

Another embodiment of the present invention includes a recombinant vector, which includes at least one isolated nucleic acid molecule of the present invention inserted into any vector capable of delivering the nucleic acid molecule into a host cell. Such a vector contains heterologous nucleic acid sequences, that is, nucleic acid sequences that are not naturally found adjacent to nucleic acid molecules of the present invention, and that preferably are derived from a species other than the species from which the nucleic acid molecule(s) are derived. The vector can be either RNA or DNA, either prokaryotic or eukaryotic, and typically is a virus or a plasmid. Recombinant vectors can be used to clone, sequence, or otherwise manipulate a parasitic helminth cuticlin nucleic acid molecule of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. An expression vector can be either prokaryotic or eukaryotic, and is typically a virus or a plasmid. An expression vector of the present invention includes any vector that functions (i.e., directs gene expression) in a recombinant cell of the present invention, including in a bacterial, fungal, parasite, insect, other animal, or plant cell. A preferred expression vector of the present invention can direct gene expression in a bacterial, yeast, helminth or other parasite, insect or mammalian cell, or more preferably in a cell type disclosed herein.

In particular, an expression vector of the present invention contains regulatory sequences such as transcription control sequences, translation control sequences, origins of replication, and other regulatory sequences that are compatible with the recombinant cell and that control the expression of a nucleic acid molecule of the present invention. In particular, a recombinant molecule of the present invention includes transcription control sequences. Transcription control sequences are sequences which control the initiation, elongation, and termination of transcription. Particularly important transcription control sequences are those which control transcription initiation, such as promoter, enhancer, operator and repressor sequences. A suitable transcription control sequence includes any transcription control sequence that can function in at least one of the recombinant cells of the present invention. A variety of such transcription control sequences are known to those skilled in the art. Preferred transcription control sequences include those which function in bacterial, yeast, helminth or other parasite, insect or mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus,—*Heliothis zea* insect virus, vaccinia virus, herpesvirus, raccoon poxvirus, other poxvirus, adenovirus, cytomegalovirus (such as immediate early promoters), picornavirus, simian virus 40, retrovirus, actin, retroviral long terminal repeat, Rous sarcoma virus, heat shock, phosphate or nitrate transcription control sequences; as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins).

Transcription control sequences of the present invention can also include naturally occurring transcription control sequences naturally associated with parasitic helminths, such as *D immitis* or *B. malayi*.

Suitable and preferred nucleic acid molecules to include in a recombinant vector of the present invention are as disclosed herein. Preferred nucleic acid molecules to include in a recombinant vector, and particularly in a recombinant molecule, include nDiCut-1A, nDiCut-1B, or nBmCut-1A, the production of which are described in the Examples section.

A recombinant molecule of the present invention may also (a) contain a secretory signal (i.e., a signal segment nucleic acid sequence) to enable an expressed cuticlin protein of the present invention to be secreted from the cell that produces the protein or (b) contain a fusion sequence which leads to the expression of a nucleic acid molecule of the present invention as a fusion protein. Examples of suitable signal segments include any signal segment capable of directing the secretion of a protein of the present invention. Preferred signal segments include, but are not limited to, native parasitic helminth signal segments, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. A eukaryotic recombinant molecule may also include intervening and/or untranslated sequences surrounding and/or within the nucleic acid sequence of the nucleic acid molecule of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ, or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include cuticlin nucleic acid molecules disclosed herein. Particularly preferred nucleic acid molecules with which to transform a cell include nDiCut-1A, nDiCut-1B, and nBmCut-1A.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention or encoding other proteins useful in the production of multivalent vaccines). A recombinant cell of the present invention can be endogenously (i.e., naturally) capable of producing a parasitic helminth cuticlin protein of the present invention or can be capable of producing such a protein after being transformed with at least one nucleic acid molecule of the present invention. A host cell of the present invention can be any cell capable of producing at least one protein of the present invention, and can be a bacterial, fungal (including yeast), parasite (including helminth, protozoa and ectoparasite), other insect, other animal or plant cell. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby Canine Kidney cells), CRFK cells (Crandell Feline Kidney cells), BSC-1 cells (African monkey kidney cell line used, for example, to culture poxviruses), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1$_x$3987 and SR-11 $_x$4072; *Spodoptera frugiperda*; *Trichoplusia ni*; BHK cells; MDCK cells; CRFK cells; BSC-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell of the present invention includes any cell transformed with at least one of any nucleic acid molecule of the present invention. Suitable and preferred nucleic acid molecules as well as suitable and preferred recombinant molecules with which to transform such a cell are disclosed herein.

In one embodiment, a recombinant cell of the present invention can be co-transformed with a recombinant molecule including a parasitic helminth cuticlin nucleic acid molecule encoding a protein of the present invention and a nucleic acid molecule encoding another protective compound, as disclosed herein (e.g., to produce multivalent vaccines).

Recombinant DNA technologies can be used to improve expression of a transformed nucleic acid molecule by manipulating, for example, the number of copies of the nucleic acid molecule within a host cell, the efficiency with which that nucleic acid molecule is transcribed, the efficiency with which the resultant transcript is translated, and the efficiency of post-translational modifications. Recombinant techniques useful for increasing the expression of a nucleic acid molecule of the present invention include, but are not limited to, operatively linking the nucleic acid molecule to a high-copy number plasmid, integration of the nucleic acid molecule into one or more host cell chromosomes, addition of vector stability sequences to a plasmid, substitution or modification of transcription control signals (e.g., promoters, operators, enhancers), substitution or modification of translational control signals (e.g., ribosome binding sites, Shine-Dalgarno sequences, or Kozak sequences), modification of a nucleic acid molecule of the present invention to correspond to the codon usage of the host cell, deletion of sequences that destabilize transcripts, and the use of control signals that temporally separate recombinant cell growth from recombinant enzyme production during fermentation. The activity of an expressed recombinant protein of the present invention may be improved by fragmenting, modifying, or derivatizing a nucleic acid molecule encoding such a protein.

Isolated parasitic helminth cuticlin proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a parasitic helminth cuticlin protein of the present invention. Such a medium typically comprises an aqueous base having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a given recombinant cell. Such culturing conditions are within the expertise of one of ordinary skill in the art. Examples of suitable conditions are included in the Examples section.

Depending on the vector and host system used for production, a resultant protein of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refer to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic helminth cuticlin protein of the present invention or a mimetope thereof (e.g., anti-parasitic helminth cuticlin antibodies). As used herein, the term "selectively binds to" a cuticlin protein refers to the ability of an antibody of the present invention to preferentially bind to specified proteins and mimetopes thereof of the present invention. Binding can be measured using a variety of methods standard in the art including enzyme immunoassays (e.g., ELISA), immunoblot assays, etc. See, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-parasitic helminth cuticlin antibody preferably selectively binds to a parasitic helminth cuticlin protein in such a way as to reduce the activity of that protein.

Isolated antibodies of the present invention can include antibodies in serum, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce cuticlin proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths or (c) as tools to screen expression libraries or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. A therapeutic composition of the present invention includes an excipient and at least one of the following protective compounds: an isolated native parasitic helminth cuticlin protein; an isolated non-native parasitic helminth cuticlin protein; a mimetope of a parasitic helminth cuticlin protein; an isolated parasitic helminth cuticlin nucleic acid molecule; an isolated antibody that selectively binds to a parasitic helminth cuticlin protein; or an inhibitor of cuticlin protein activity identified by its ability to inhibit parasitic helminth cuticlin activity. As used herein, a protective compound refers to a compound that, when administered to an animal in an effective manner, is able to treat, ameliorate, or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth cuticlin-based compound of the present invention in combination with at least one additional compound protective against one or more infectious agents. Examples of such compounds and infectious agents are disclosed herein.

A therapeutic composition of the present invention can be administered to any animal susceptible to such therapy, preferably to mammals, and more preferably to dogs, cats, humans, ferrets, horses, cattle, sheep and other pets, work animals, economic food animals, or zoo animals. Preferred animals to protect against heartworm disease include dogs, cats, humans and ferrets, with dogs and cats being particularly preferred.

In one embodiment, a therapeutic composition of the present invention can be administered to the vector in which the parasitic helminth develops, such as to a mosquito, in order to prevent the spread of parasitic helminth to the definitive mammalian host. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal,—or o-cresol, formalin, and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleuklin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g. MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research. Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphores, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about month, more preferably for at least about 3 months, even more preferably for at least about 6 months, even more preferably for at least about 9 months, and even more preferably for at least about 12 months.

In order to protect an animal from disease caused by a parasitic helminth, a therapeutic composition of the present invention is administered to the animal in an effective manner such that the composition is capable of protecting that animal from a disease caused by a parasitic helminth. For example, an isolated protein or mimetope thereof is administered in an amount and manner that elicits (i.e., stimulates) an immune response that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. An oligonucleotide nucleic acid molecule of the present invention can also be administered in an effective manner, thereby reducing expression of native parasitic helminth cuticlin proteins in order to interfere with development of the parasitic helminths targeted in accordance with the present invention.

Therapeutic compositions of the present invention can be administered to animals prior to infection in order to prevent infection (i.e., as a preventative vaccine) or can be administered to animals after infection in order to treat disease caused by the parasitic helminth (i.e., as a curative agent or a therapeutic vaccine).

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope, or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, and intramuscular routes.

According to one embodiment, a nucleic acid molecule of the present invention can be administered to an animal in a fashion to enable expression of that nucleic acid molecule into a protective protein or protective RNA (e.g., an anti-sense RNA, a ribozyme, a triple helix form, or an RNA drug) in the animal. Nucleic acid molecules can be delivered to an animal by a variety of methods including, but not limited to, (a) administering a genetic vaccine (e.g., a naked DNA or RNA molecule, such as is taught, for example, in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. A preferred genetic vaccine includes at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of "strong" poly(A) sequences is also preferred.

A genetic vaccine of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 500 μg, depending on the route of administration or method of delivery, as can be determined by those skilled in the art. Suitable delivery methods include, for example, by injection, as drops, aerosolized, or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, picornaviruses, and species-specific herpesviruses. Methods to produce and use a recombinant alphavirus vaccine are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising a parasitic helminth cuticlin nucleic acid molecule of the present invention is administered according to a protocol that results in the animal producing a sufficient immune response to protect itself from heartworm disease. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes a recombinant cell of the present invention that expresses at least one protein of the present invention. Preferred recombinant cells for this embodiment include Salmonella, E. coli, Listeria, Mycobacterium, S. frugiperda, yeast (including Saccharomyces cerevisiae and Pichia pastoris), BHK, BSC-1, myoblast G8, COS (e.g., COS-7), Vero, MDCK or CRFK recombinant cells. A recombinant cell vaccine of the present invention can be administered in a variety of ways but has the advantage that it can be administered orally, preferably at doses ranging from about $10^8$ to about $10^{12}$ cells per kilogram body weight. Administration protocols are similar to those described herein for protein-based vaccines. A recombinant cell vaccine can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of parasitic helminth cuticlin proteins, nucleic acid molecules, antibodies or inhibitory compounds of the present invention to protect an animal from heartworm disease. It is particularly preferred to prevent L3 that are delivered to the animal by the mosquito intermediate host from maturing into adult worms. Accordingly, a preferred therapeutic composition is one that is able to inhibit at least one step in the portion of the parasite's development cycle that includes L3, third molt, L4, fourth molt, and immature adult prior to entering the circulatory system. In dogs, this portion of the developmental cycle is about 70 days in length. A particularly preferred therapeutic composition includes a parasitic helminth cuticlin-based therapeutic composition of the present invention, particularly in light of the evidence herein reported that cuticlin is expressed in both larval and adult stages of the parasite. Such a composition can include a parasitic helminth cuticlin nucleic acid molecule, a parasitic helminth cuticlin protein or a mimetope thereof, anti-parasitic helminth cuticlin antibodies, or inhibitors of parasitic helminth cuticlin activity. Such therapeutic compositions are administered to an animal in a manner effective to protect the animals from heartworm disease. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of parasitic helminth cuticlin activity, i.e., a compound capable of substantially interfering with the function of a parasitic helminth cuticlin protein, also referred to herein as a cuticlin inhibitor. In one embodiment, such an inhibitor comprises a compound that interacts directly with a cuticlin protein active site (usually by binding to or modifying the active site), thereby inhibiting cuticlin activity. According to this embodiment, a cuticlin inhibitor can also interact with other regions of a cuticlin protein to inhibit cuticlin activity, for example, by allosteric interaction. Preferably, a cuticlin inhibitor of the present invention is identified by its ability to bind to, or otherwise interact with, a parasitic helminth cuticlin protein, thereby inhibiting cuticlin activity of that protein. Such a cuticlin inhibitor is a suitable for inclusion in a therapeutic composition of the present invention as long as the compound is not harmful to the host animal being treated.

A cuticlin inhibitor can be identified using a parasitic helminth cuticlin protein of the present invention. As such, one embodiment of the present invention is a method to identify a compound capable of inhibiting cuticlin activity of a parasitic helminth susceptible to inhibition by an inhibitor of parasitic helminth cuticlin activity. Such a method includes the steps of (a) contacting (e.g., combining, mixing) an isolated parasitic helminth cuticlin protein, preferably a *D. immitis* cuticlin protein, with a putative inhibitory compound under conditions in which, in the absence of the compound, the protein has cuticlin activity, and (b) determining if the putative inhibitory compound inhibits the cuticlin activity. Putative inhibitory compounds to screen include small organic molecules, antibodies (including mimetopes thereof) and substrate analogs. Methods to determine cuticlin activity are known to those skilled in the art; see, for example, Rhee. et al., ibid., Lim, et al., ibid., Sauri, et al., ibid., and Kim, et al., ibid.

The present invention also includes a test kit to identify a compound capable of inhibiting cuticlin activity of a parasitic helminth. Such a test kit includes an isolated parasitic helminth cuticlin protein, preferably a *D. immitis* cuticlin protein, having cuticlin activity, and a means for determining the extent of inhibition of cuticlin activity in the presence of (i.e., effected by) a putative inhibitory compound. Such compounds are also screened to identify those that are substantially not toxic in host animals, e.g., compounds that do not inhibit the activity of mammalian cuticlin.

Cuticlin inhibitors isolated by such a method or test kit can be used to inhibit any parasitic helminth cuticlin protein that is susceptible to such an inhibitor. A particularly preferred cuticlin inhibitor of the present invention is capable of protecting an animal from heartworm disease. A therapeutic composition comprising a compound that inhibits cuticlin activity can be administered to an animal in an effective manner to protect that animal from disease caused by the parasite expressing the targeted cuticlin enzyme, and preferably to protect that animal from heartworm disease. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect specific phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are *D. immitis* or *B. malayi*.

A Sequence Listing pursuant to 37 CFR §1.821 is submitted herewith on separately numbered pages. A copy in computer readable form is also submitted herewith. Applicants assert pursuant to 37 CFR §1.821(f) that the content of the paper and computer readable copies of SEQ ID NO:1 through SEQ ID NO:18 submitted herewith are the same.

The following examples are provided for the purposes of illustration and are not intended to limit the scope of the present invention.

EXAMPLES

It is to be noted that these Examples include a number of molecular biology, microbiology, immunology and biochemistry techniques familiar to those skilled in the art. Disclosure of such techniques can be found, for example, in Sambrook et al., ibid., Ausubel, et al.,1993, *Current Protocols in Molecular Biology*, Greene/Wiley Interscience, New York, N.Y., and related references. Ausubel, et al, ibid. is incorporated by reference herein in its entirety. DNA and protein sequence analyses were carried out using the PC/GENE™ sequence analysis program, version 6.60 (available from Intelligenetics, Inc., Mountainview, Calif.). The settings for analysis were as follows. NAlign:(nucleic acid)open gap cost 10; unit gap cost −10; Palign(protein): open gap cost −2, unit gap cost −2; CLUSTAL: Protein, K-triple for protein=1, Gap penalty=10, Window size=10; Nucleic acid, K-triple for nucleic acids=5;filtering level= 2.5; Parameter for final alignment: Open gap cost=10, Unit gap cost=10; Transitions are WEIGHTED twice as likely as transversions. It should also be noted that, because nucleic-acid sequencing technology, and in particular the sequencing of PCR products, is not entirely error-free, the nucleic acid and deduced protein sequences presented herein represent apparent nucleic acid sequences of the nucleic acid molecules encoding parasitic helminth cuticlin proteins of the present invention.

Example 1

This example describes the molecular cloning of two related cuticlin genes from *Dirofilaria immitis*, referred to herein as DiCut-1A and DiCut-1B. As is herein described, DiCut-1A and DiCut-1B are related to the cut-1 cuticlin genes from Ascaris and *C. elegans*. Despite this relatedness, initial attempts to isolate genes encoding cuticlin proteins from *D. immitis* using degenerate primers based on *C. elegans* and Ascaris cut-1 were unsuccessful. Subsequent to the unsuccessful attempts to isolate cuticlin genes from *D. immitis* based on homology to the Ascaris and *C. elegans* cut-1 cuticlin genes, *D. immitis* cDNA sequences with homology to the Ascaris and *C. elegans* cut-1 genes were identified from a *D. immitis* larval EST DNA sequence, as follows.

*D. immitis* larval cDNA was produced and enriched for DNA representing larval message in relation to adult message using a CLONTECH PCR-Select™ cDNA subtraction kit (available from CLONETECH, Palo Alto, Calif.) according to the manufacturer's instructions. These larval cDNAs were subcloned into the pCRII™ vector (available from Invitrogen, San Diego, Calif.) according to the manufacturer's instructions. The isolated and subcloned larval cDNAs were sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following the standard protocol. Samples were resuspended according to ABI protocols and were run on a Perkin-Elmer ABI PRISM™ 377 Automated DNA Sequencer.

The first EST sequence obtained represented a *D. immitis* cuticlin nucleic acid molecule 1016 bp long. This sequence comprises the nucleic acid sequence between base pairs 194 and 1210 of the essentially full-length cDNA sequence of a *D. immitis* cuticlin nucleic acid molecule referred to herein as nDiCut-1A (the coding and complementary strands of which are herein represented by SEQ ID NO:1 and SEQ ID NO:2, respectively). A second *D. immitis* cuticlin EST fragment was obtained which overlapped with the previous EST fragment at the 3' end, and contributed an additional 569 base pairs of sequence comprising the nucleotide sequence between base pairs 1211 and 1779 of nDiCut-1A (SEQ ID NO:1). In order to obtain the 5' end of nDiCut-1A, and to confirm the sequence of the 3' end of the molecule, sense and antisense primers specific to the *D. immitis* cuticlin EST sequence were designed to hybridize to nDiCut-1A between base pairs 862 and 895 of the final nDiCut-1A sequence (SEQ ID NO:1). The sense primer specific to the EST, referred to herein as CUT-3'R (SEQ ID NO:11), consists of the sequence: 5' G GCT GGC CAA GAA GCT CAC GTA TAC AAA TAT GCG 3'. The antisense primer referred to herein as CUT-5'R (SEQ ID NO:12), consists of the sequence: 5' CGC ATA TTT GTA TAC GTG AGC TTC TTG GCC AGC C 3'. The 5' end of the cuticlin EST nucleic acid molecule was amplified by standard RT-PCR methods from *D. immitis* L3-48 hr first-strand cDNA using the nematode 22-bp splice leader sequence, referred to herein as SL1 (5' GGTTTAATTA CCCAAGTTTG AG 3'; SEQ ID NO:13) and the EST-specific antisense primer (SEQ ID NO:12). The RT-PCR reaction generated an 895 bp product. The composite full length cDNA sequence of nDiCut-1A comprises a 1779 bp nucleic acid molecule (the coding and complementary strands of which are herein represented by SEQ ID NO:1 and SEQ ID NO:2, respectively). nDiCut-1A encodes a 387 amino acid protein (herein referred to as PDiCut-1A, represented by SEQ ID NO:4).

RT-PCR using SL1 (SEQ ID NO:13) and the EST-specific antisense primer, CUT-5'R (SEQ ID NO:12) was also carried out using *Brugia malayi* adult female cDNA as a template. This reaction resulted in a partial 5' end product of a Brugia cuticlin homolog, referred to herein as nBmcut-1A (the coding strand and reverse complement of which are herein represented by SEQ ID NO:16 and SEQ ID NO:18, respectively). nBmCut-1A encodes a 245 amino acid protein herein referred to as PBmCut-1A, represented by SEQ ID NO:17).

In order to confirm the sequence of the 3' nDiCut-1A EST fragment, 3' RACE PCR was performed using a Marathon™ cDNA Amplification Kit (available from CLONTECH) according to the manufacturer's instructions. The template for amplification was *D. immitis* adult female first-strand cDNA and amplification was performed using the EST-specific sense primer, CUT-3'R (SEQ ID NO:11) and an antisense RACE-adapter primer (5' CCA TCC TAA TAC GAC TCA CTA TAG GGC 3', referred to herein as SEQ ID NO:14). Instead of obtaining a product of the predicted size of 919 bp (as would be expected if the amplified product represented nDiCut-1A sequence), a 643 bp nucleic acid molecule was obtained, This molecule represented the 3' end of an additional *D. immitis* cuticlin nucleic acid molecule referred to herein as nDiCut-1B. The 3' sequence of nDiCut-1B was very different from the sequence already determined for the 3' end of nDiCut-1A. The 5' end of nDiCut-1B was amplified by SL1 RT-PCR using an nDiCut-1B specific antisense primer. This DiCut-1B primer, referred to as CUTb, consists of the sequence: GGT TAT ATC AAC CGT GCT AAA ACC GGT ACT GAC GTC CAC CG (herein referred to as SEQ ID NO:15), and represents the nucleic acid sequence located between base pairs 981 and 1020 of the essentially full-length nDiCut-1B cDNA sequence (SEQ ID NO:6). RT-PCR using CUTb and SL1 as primers generated a 1020 bp nDiCut-1B sequence when either larval or adult first-strand cDNA was used as the template. The composite full length cDNA sequence of nDiCut-1B comprises 1372 bp, herein represented by SEQ ID NO:6 (the coding strand) and SEQ ID NO:7 (the reverse complement). nDiCut-1B encodes a 271 amino acids (herein referred to as PDiCut-1B, represented by SEQ ID NO:9).

RT-PCR reactions were carried out on total RNA prepared from 0-hr L3, 48-hr L3, 6-day L4, male and female adult worms using cuticlin-specific primers. The results indicate that gene expression for both isoforms of cuticlin were up-regulated prior to the molt, with maximal transcription at 48 hr-L3 and minimal expression at 0 hr and 6-day L4. There was detectable expression of both genes in male and female adult worms.

A homology search of a non-redundant protein database was performed with SEQ ID NO:4, using the BLASTX program available through the BLAST™ network of the National Center for Biotechnology Information (NCBI) (National Library of Medicine, National Institutes of Health, Baltimore, Md.), available on the World Wide Web. This analysis showed that DiCut-1A had significant homology to Ascaris cut-1 precursor at the amino acid level (bases 200 through 988 of SEQ ID NO:1 encode an amino acid sequence that has 91% identity with the Ascaris cut-1 precursor), and nucleotides 434 through 880 of DiCut-1B encode an amino acid sequence that has 81% identity to the same Ascaris homolog.

Both Dirofilaria cuticlin cDNAs were expressed in a λ-cro expression vector. DiCut-1A was expressed as a 44.5 kD histidine fusion protein, and DiCut-1B was expressed as a 31.1 kD fusion protein. Antibodies raised to larval cuticles in rabbit and sera from a rabbit immunized with trickle doses of L3 stage larvae immunoreact with both forms of cuticlin.

DiCut-1A and DiCut-1B cDNAs were used to probe Southern blots of genomic DNA from adult *D. immitis*. Both cDNAs hybridized to two almost identical genomic fragments suggesting that DiCut-1A and DiCut-1B are each encoded by a single copy gene. Because DiCut-1A and DiCut-1B are 75% identical at the nucleotide level, it is likely that each cDNA may hybridize to the other gene, as was seen in the present study. Interestingly, the DiCut-1A and DiCut-1B cDNA probes, were not cut internally by EcoRI, but did hybridize to a number of fragments in genomic DNA digested with EcoRI. These results suggest the presence of introns within the cuticlin genes.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated *Dirofilaria immitis* protein comprising an amino acid sequence SEQ ID NO:4.

2. A composition comprising an excipient and an isolated *Dirofilaria immitis* protein comprising an amino acid sequence SEQ ID NO:4.

* * * * *